(12) United States Patent
Pekar et al.

(10) Patent No.: US 11,687,688 B2
(45) Date of Patent: Jun. 27, 2023

(54) APPROACH FOR AFTERTREATMENT SYSTEM MODELING AND MODEL IDENTIFICATION

(71) Applicant: Garrett Transportation I Inc., Torrance, CA (US)

(72) Inventors: Jaroslav Pekar, Pacov (CZ); Gregory Stewart, North Vancouver (CA); Ondrej Santin, Svijany (CZ); Daniel Pachner, Prague (CZ)

(73) Assignee: Garrett Transportation I Inc., Torrance, CA (US)

( * ) Notice: Subject to any disclaimer, the term of this patent is extended or adjusted under 35 U.S.C. 154(b) by 422 days.

(21) Appl. No.: 16/824,244

(22) Filed: Mar. 19, 2020

(65) Prior Publication Data
US 2020/0218837 A1    Jul. 9, 2020

Related U.S. Application Data

(62) Division of application No. 15/019,029, filed on Feb. 9, 2016, now Pat. No. 10,621,291.

(51) Int. Cl.
*G06F 30/20* (2020.01)
*F02D 41/24* (2006.01)
(Continued)

(52) U.S. Cl.
CPC .............. *G06F 30/20* (2020.01); *F01N 11/00* (2013.01); *F02D 41/2432* (2013.01);
(Continued)

(58) Field of Classification Search
CPC .. F02D 41/2432; F02D 41/26; F02D 41/1445; F02D 41/1446; F02D 41/1448;
(Continued)

(56) References Cited

U.S. PATENT DOCUMENTS

| 3,744,461 A | 7/1973 | Davis |
| 4,005,578 A | 2/1977 | McInerney |

(Continued)

FOREIGN PATENT DOCUMENTS

| CN | 102063561 | 5/2011 |
| CN | 102331350 | 1/2012 |

(Continued)

OTHER PUBLICATIONS

"Aftertreatment Modeling of RCCI Engine During Transient Operation," University of Wisconsin—Engine Research Center, 1 page, May 31, 2014.

(Continued)

*Primary Examiner* — John Kwon
*Assistant Examiner* — Johnny H Hoang
(74) *Attorney, Agent, or Firm* — Seager, Tufte & Wickhem, LLP

(57) ABSTRACT

A system and approach for catalyst model parameter identification with modeling accomplished by an identification procedure that may incorporate a catalyst parameter identification procedure which may include determination of parameters for a catalyst device, specification of values for parameters and component level identification. Component level identification may be of a thermal model, adsorption and desorption, and chemistry. There may then be system level identification to get a final estimate of catalyst parameters.

6 Claims, 32 Drawing Sheets

(51) Int. Cl.
*F02D 41/26* (2006.01)
*F01N 11/00* (2006.01)
*G05B 17/00* (2006.01)
F02D 41/14 (2006.01)
G01M 15/10 (2006.01)
G06F 119/08 (2020.01)
G01N 33/00 (2006.01)

(52) U.S. Cl.
CPC ............. *F02D 41/26* (2013.01); *G05B 17/00* (2013.01); *F01N 2260/24* (2013.01); *F01N 2550/03* (2013.01); *F02D 41/1445* (2013.01); *F02D 41/1446* (2013.01); *F02D 41/1448* (2013.01); *F02D 41/1459* (2013.01); *F02D 41/1461* (2013.01); *F02D 2041/1415* (2013.01); *F02D 2041/1433* (2013.01); *F02D 2041/1437* (2013.01); *F02D 2041/1469* (2013.01); *F02D 2200/08* (2013.01); *G01M 15/102* (2013.01); *G01N 2033/0068* (2013.01); *G06F 2119/08* (2020.01); *Y02T 10/40* (2013.01)

(58) Field of Classification Search
CPC ............. F02D 41/1459; F02D 41/1461; F02D 2041/1415; F02D 2041/1433; F02D 2041/1437; F02D 2041/1469; F02D 2200/08; F01N 11/00; F01N 2260/24; F01N 2550/03; G06F 17/5009
See application file for complete search history.

(56) References Cited

U.S. PATENT DOCUMENTS

| | | |
|---|---|---|
| 4,055,158 A | 10/1977 | Marsee |
| 4,206,606 A | 6/1980 | Yamada |
| 4,252,098 A | 2/1981 | Tomczak et al. |
| 4,359,991 A | 11/1982 | Stumpp et al. |
| 4,383,441 A | 5/1983 | Willis et al. |
| 4,426,982 A | 1/1984 | Lehner et al. |
| 4,438,497 A | 3/1984 | Willis et al. |
| 4,440,140 A | 4/1984 | Kawagoe et al. |
| 4,456,883 A | 6/1984 | Bullis et al. |
| 4,485,794 A | 12/1984 | Kimberley et al. |
| 4,601,270 A | 7/1986 | Kimberley et al. |
| 4,616,308 A | 10/1986 | Morshedi et al. |
| 4,653,449 A | 3/1987 | Kamei et al. |
| 4,671,235 A | 6/1987 | Hosaka |
| 4,677,559 A | 6/1987 | Van Bruck |
| 4,735,181 A | 4/1988 | Kaneko et al. |
| 4,947,334 A | 8/1990 | Massey et al. |
| 4,962,570 A | 10/1990 | Hosaka et al. |
| 5,044,337 A | 9/1991 | Williams |
| 5,076,237 A | 12/1991 | Hartman et al. |
| 5,089,236 A | 2/1992 | Clerc |
| 5,094,213 A | 3/1992 | Dudek et al. |
| 5,095,874 A | 3/1992 | Schnaibel et al. |
| 5,108,716 A | 4/1992 | Nishizawa |
| 5,123,397 A | 6/1992 | Richeson |
| 5,150,289 A | 9/1992 | Badavas |
| 5,186,081 A | 2/1993 | Richardson et al. |
| 5,233,829 A | 8/1993 | Komatsu |
| 5,270,935 A | 12/1993 | Dudek et al. |
| 5,273,019 A | 12/1993 | Matthews et al. |
| 5,282,449 A | 2/1994 | Takahashi et al. |
| 5,293,553 A | 3/1994 | Dudek et al. |
| 5,349,816 A | 9/1994 | Sanbayashi et al. |
| 5,365,734 A | 11/1994 | Takeshima |
| 5,394,322 A | 2/1995 | Hansen |
| 5,394,331 A | 2/1995 | Dudek et al. |
| 5,398,502 A | 3/1995 | Watanabe |
| 5,408,406 A | 4/1995 | Mathur et al. |
| 5,431,139 A | 7/1995 | Grutter et al. |
| 5,452,576 A | 9/1995 | Hamburg et al. |
| 5,477,840 A | 12/1995 | Neumann |
| 5,560,208 A | 10/1996 | Halimi et al. |
| 5,570,574 A | 11/1996 | Yamashita et al. |
| 5,598,825 A | 2/1997 | Neumann |
| 5,609,139 A | 3/1997 | Ueda et al. |
| 5,611,198 A | 3/1997 | Lane et al. |
| 5,682,317 A | 10/1997 | Keeler et al. |
| 5,690,086 A | 11/1997 | Kawano et al. |
| 5,692,478 A | 12/1997 | Nogi et al. |
| 5,697,339 A | 12/1997 | Esposito |
| 5,704,011 A | 12/1997 | Hansen et al. |
| 5,740,033 A | 4/1998 | Wassick et al. |
| 5,746,183 A | 5/1998 | Parke et al. |
| 5,765,533 A | 6/1998 | Nakajima |
| 5,771,867 A | 6/1998 | Amstutz et al. |
| 5,785,030 A | 7/1998 | Paas |
| 5,788,004 A | 8/1998 | Friedmann et al. |
| 5,842,340 A | 12/1998 | Bush et al. |
| 5,846,157 A | 12/1998 | Reinke et al. |
| 5,893,092 A | 4/1999 | Driscoll |
| 5,917,405 A | 6/1999 | Joao |
| 5,924,280 A | 7/1999 | Tarabulski |
| 5,942,195 A | 8/1999 | Lecea et al. |
| 5,964,199 A | 10/1999 | Atago et al. |
| 5,970,075 A | 10/1999 | Wasada |
| 5,974,788 A | 11/1999 | Hepburn et al. |
| 5,995,895 A | 11/1999 | Watt et al. |
| 6,029,626 A | 2/2000 | Bruestle |
| 6,035,640 A | 3/2000 | Kolmanovsky et al. |
| 6,048,620 A | 4/2000 | Zhong |
| 6,048,628 A | 4/2000 | Hillmann et al. |
| 6,055,810 A | 5/2000 | Borland et al. |
| 6,056,781 A | 5/2000 | Wassick et al. |
| 6,058,700 A | 5/2000 | Yamashita et al. |
| 6,067,800 A | 5/2000 | Kolmanovsky et al. |
| 6,076,353 A | 6/2000 | Fruedenberg et al. |
| 6,105,365 A | 8/2000 | Deeba et al. |
| 6,122,555 A | 9/2000 | Lu |
| 6,134,883 A | 10/2000 | Kato et al. |
| 6,153,159 A | 11/2000 | Engeler et al. |
| 6,161,528 A | 12/2000 | Akao et al. |
| 6,170,259 B1 | 1/2001 | Boegner et al. |
| 6,171,556 B1 | 1/2001 | Burk et al. |
| 6,178,743 B1 | 1/2001 | Hirota et al. |
| 6,178,749 B1 | 1/2001 | Kolmanovsky et al. |
| 6,208,914 B1 | 3/2001 | Ward et al. |
| 6,216,083 B1 | 4/2001 | Ulyanov et al. |
| 6,233,922 B1 | 5/2001 | Maloney |
| 6,236,956 B1 | 5/2001 | Mantooth et al. |
| 6,237,330 B1 | 5/2001 | Takahashi et al. |
| 6,242,873 B1 | 6/2001 | Drozdz et al. |
| 6,263,672 B1 | 7/2001 | Roby et al. |
| 6,273,060 B1 | 8/2001 | Cullen |
| 6,279,551 B1 | 8/2001 | Iwano et al. |
| 6,312,538 B1 | 11/2001 | Latypov et al. |
| 6,314,351 B1 | 11/2001 | Chutorash |
| 6,314,662 B1 | 11/2001 | Ellis, III |
| 6,314,724 B1 | 11/2001 | Kakuyama et al. |
| 6,321,538 B2 | 11/2001 | Hasler |
| 6,327,361 B1 | 12/2001 | Harshavardhana et al. |
| 6,338,245 B1 | 1/2002 | Shimoda et al. |
| 6,341,487 B1 | 1/2002 | Takahashi et al. |
| 6,347,619 B1 | 2/2002 | Whiting et al. |
| 6,360,159 B1 | 3/2002 | Miller et al. |
| 6,360,541 B2 | 3/2002 | Waszkiewicz et al. |
| 6,360,732 B1 | 3/2002 | Bailey et al. |
| 6,363,715 B1 | 4/2002 | Bidner et al. |
| 6,363,907 B1 | 4/2002 | Arai et al. |
| 6,379,281 B1 | 4/2002 | Collins et al. |
| 6,389,203 B1 | 5/2002 | Jordan et al. |
| 6,389,803 B1 | 5/2002 | Sumilla et al. |
| 6,425,371 B2 | 7/2002 | Majima |
| 6,427,436 B1 | 8/2002 | Allansson et al. |
| 6,431,160 B1 | 8/2002 | Sugiyama et al. |
| 6,445,963 B1 | 9/2002 | Blevins et al. |
| 6,446,430 B1 | 9/2002 | Roth et al. |
| 6,453,308 B1 | 9/2002 | Zhao et al. |
| 6,463,733 B1 | 10/2002 | Asik et al. |
| 6,463,734 B1 | 10/2002 | Tamura et al. |

(56) References Cited

U.S. PATENT DOCUMENTS

| | | |
|---|---|---|
| 6,466,893 B1 | 10/2002 | Latwesen et al. |
| 6,470,682 B2 | 10/2002 | Gray, Jr. |
| 6,470,862 B2 | 10/2002 | Isobe et al. |
| 6,470,886 B1 | 10/2002 | Jestrabek-Hart |
| 6,481,139 B2 | 11/2002 | Weldle |
| 6,494,038 B2 | 12/2002 | Kobayashi et al. |
| 6,502,391 B1 | 1/2003 | Hirota et al. |
| 6,510,351 B1 | 1/2003 | Blevins et al. |
| 6,512,974 B2 | 1/2003 | Houston et al. |
| 6,513,495 B1 | 2/2003 | Franke et al. |
| 6,532,433 B2 | 3/2003 | Bharadwaj et al. |
| 6,542,076 B1 | 4/2003 | Joao |
| 6,546,329 B2 | 4/2003 | Bellinger |
| 6,549,130 B1 | 4/2003 | Joao |
| 6,550,307 B1 | 4/2003 | Zhang et al. |
| 6,553,754 B2 | 4/2003 | Meyer et al. |
| 6,560,528 B1 | 5/2003 | Gitlin et al. |
| 6,560,960 B2 | 5/2003 | Nishimura et al. |
| 6,571,191 B1 | 5/2003 | York et al. |
| 6,579,206 B2 | 6/2003 | Liu et al. |
| 6,591,605 B2 | 7/2003 | Lewis |
| 6,594,990 B2 | 7/2003 | Kuenstler et al. |
| 6,601,387 B2 | 8/2003 | Zurawski et al. |
| 6,612,293 B2 | 9/2003 | Schweinzer et al. |
| 6,615,584 B2 | 9/2003 | Ostertag |
| 6,625,978 B1 | 9/2003 | Eriksson et al. |
| 6,629,408 B1 | 10/2003 | Murakami et al. |
| 6,637,382 B1 | 10/2003 | Brehob et al. |
| 6,644,017 B2 | 11/2003 | Takahashi et al. |
| 6,647,710 B2 | 11/2003 | Nishiyama et al. |
| 6,647,971 B2 | 11/2003 | Vaughan et al. |
| 6,651,614 B2 | 11/2003 | Flamig-Vetter et al. |
| 6,662,058 B1 | 12/2003 | Sanchez |
| 6,666,198 B2 | 12/2003 | Mitsutani |
| 6,666,410 B2 | 12/2003 | Boelitz et al. |
| 6,671,603 B2 | 12/2003 | Cari et al. |
| 6,672,052 B2 | 1/2004 | Taga et al. |
| 6,672,060 B1 | 1/2004 | Buckland et al. |
| 6,679,050 B1 | 1/2004 | Takahashi et al. |
| 6,687,597 B2 | 2/2004 | Sulatisky et al. |
| 6,688,283 B2 | 2/2004 | Jaye |
| 6,694,244 B2 | 2/2004 | Meyer et al. |
| 6,694,724 B2 | 2/2004 | Tanaka et al. |
| 6,705,084 B2 | 3/2004 | Allen et al. |
| 6,718,254 B2 | 4/2004 | Hashimoto et al. |
| 6,718,753 B2 | 4/2004 | Bromberg et al. |
| 6,725,208 B1 | 4/2004 | Hartman et al. |
| 6,736,120 B2 | 5/2004 | Surnilla |
| 6,738,682 B1 | 5/2004 | Pasadyn |
| 6,739,122 B2 | 5/2004 | Kitajima et al. |
| 6,742,330 B2 | 6/2004 | Genderen |
| 6,743,352 B2 | 6/2004 | Ando et al. |
| 6,748,936 B2 | 6/2004 | Kinomura et al. |
| 6,752,131 B2 | 6/2004 | Poola et al. |
| 6,752,135 B2 | 6/2004 | McLaughlin et al. |
| 6,757,579 B1 | 6/2004 | Pasadyn |
| 6,758,037 B2 | 7/2004 | Terada et al. |
| 6,760,631 B1 | 7/2004 | Berkowitz et al. |
| 6,760,657 B2 | 7/2004 | Katoh |
| 6,760,658 B2 | 7/2004 | Yasui et al. |
| 6,770,009 B2 | 8/2004 | Badillo et al. |
| 6,772,585 B2 | 8/2004 | Iihoshi et al. |
| 6,775,623 B2 | 8/2004 | Ali et al. |
| 6,779,344 B2 | 8/2004 | Hartman et al. |
| 6,779,512 B2 | 8/2004 | Mitsutani |
| 6,788,072 B2 | 9/2004 | Nagy et al. |
| 6,789,533 B1 | 9/2004 | Hashimoto et al. |
| 6,792,927 B2 | 9/2004 | Kobayashi |
| 6,804,618 B2 | 10/2004 | Junk |
| 6,814,062 B2 | 11/2004 | Esteghlal et al. |
| 6,817,171 B2 | 11/2004 | Zhu |
| 6,823,667 B2 | 11/2004 | Braun et al. |
| 6,823,675 B2 | 11/2004 | Brunell et al. |
| 6,826,903 B2 | 12/2004 | Yahata et al. |
| 6,827,060 B2 | 12/2004 | Huh |
| 6,827,061 B2 | 12/2004 | Nytomt et al. |
| 6,827,070 B2 | 12/2004 | Fehl et al. |
| 6,834,497 B2 | 12/2004 | Miyoshi et al. |
| 6,837,042 B2 | 1/2005 | Colignon et al. |
| 6,839,637 B2 | 1/2005 | Moteki et al. |
| 6,849,030 B2 | 2/2005 | Yamamoto et al. |
| 6,873,675 B2 | 3/2005 | Kurady et al. |
| 6,874,467 B2 | 4/2005 | Hunt et al. |
| 6,879,906 B2 | 4/2005 | Makki et al. |
| 6,882,929 B2 | 4/2005 | Liang et al. |
| 6,904,751 B2 | 6/2005 | Makki et al. |
| 6,911,414 B2 | 6/2005 | Kimura et al. |
| 6,915,779 B2 | 7/2005 | Sriprakash |
| 6,920,865 B2 | 7/2005 | Lyon |
| 6,923,902 B2 | 8/2005 | Ando et al. |
| 6,925,372 B2 | 8/2005 | Yasui |
| 6,925,796 B2 | 8/2005 | Nieuwstadt et al. |
| 6,928,362 B2 | 8/2005 | Meaney |
| 6,928,817 B2 | 8/2005 | Ahmad |
| 6,931,840 B2 | 8/2005 | Strayer et al. |
| 6,934,931 B2 | 8/2005 | Plumer et al. |
| 6,941,744 B2 | 9/2005 | Tanaka |
| 6,945,033 B2 | 9/2005 | Sealy et al. |
| 6,948,310 B2 | 9/2005 | Roberts, Jr. et al. |
| 6,953,024 B2 | 10/2005 | Linna et al. |
| 6,965,826 B2 | 11/2005 | Andres et al. |
| 6,968,677 B2 | 11/2005 | Tamura |
| 6,971,258 B2 | 12/2005 | Rhodes et al. |
| 6,973,382 B2 | 12/2005 | Rodriguez et al. |
| 6,978,744 B2 | 12/2005 | Yuasa et al. |
| 6,988,017 B2 | 1/2006 | Pasadyn et al. |
| 6,990,401 B2 | 1/2006 | Neiss et al. |
| 6,996,975 B2 | 2/2006 | Radhamohan et al. |
| 7,000,379 B2 | 2/2006 | Makki et al. |
| 7,013,637 B2 | 3/2006 | Yoshida |
| 7,016,779 B2 | 3/2006 | Bowyer |
| 7,028,464 B2 | 4/2006 | Rosel et al. |
| 7,039,475 B2 | 5/2006 | Sayyarrodsari et al. |
| 7,047,938 B2 | 5/2006 | Flynn et al. |
| 7,052,434 B2 | 5/2006 | Makino et al. |
| 7,055,311 B2 | 6/2006 | Beutel et al. |
| 7,059,112 B2 | 6/2006 | Bidner et al. |
| 7,063,080 B2 | 6/2006 | Kitah et al. |
| 7,067,319 B2 | 6/2006 | Wills et al. |
| 7,069,903 B2 | 7/2006 | Surnilla et al. |
| 7,082,753 B2 | 8/2006 | Dalla Betta et al. |
| 7,085,615 B2 | 8/2006 | Persson et al. |
| 7,106,866 B2 | 9/2006 | Astorino et al. |
| 7,107,978 B2 | 9/2006 | Itoyama |
| 7,111,450 B2 | 9/2006 | Surnilla |
| 7,111,455 B2 | 9/2006 | Okugawa et al. |
| 7,113,835 B2 | 9/2006 | Boyden et al. |
| 7,117,046 B2 | 10/2006 | Boyden et al. |
| 7,124,013 B2 | 10/2006 | Yasui |
| 7,149,590 B2 | 12/2006 | Martin et al. |
| 7,151,976 B2 | 12/2006 | Lin |
| 7,152,023 B2 | 12/2006 | Das |
| 7,155,334 B1 | 12/2006 | Stewart et al. |
| 7,165,393 B2 | 1/2007 | Betta et al. |
| 7,165,399 B2 | 1/2007 | Stewart |
| 7,168,239 B2 | 1/2007 | Ingram et al. |
| 7,182,075 B2 | 2/2007 | Shahed et al. |
| 7,184,845 B2 | 2/2007 | Sayyarrodsari et al. |
| 7,184,992 B1 | 2/2007 | Polyak et al. |
| 7,188,637 B2 | 3/2007 | Dreyer et al. |
| 7,194,987 B2 | 3/2007 | Mogi |
| 7,197,485 B2 | 3/2007 | Fuller |
| 7,200,988 B2 | 4/2007 | Yamashita |
| 7,204,079 B2 | 4/2007 | Audoin |
| 7,212,908 B2 | 5/2007 | Li et al. |
| 7,275,374 B2 | 10/2007 | Stewart et al. |
| 7,275,415 B2 | 10/2007 | Rhodes et al. |
| 7,277,010 B2 | 10/2007 | Joao |
| 7,281,368 B2 | 10/2007 | Miyake et al. |
| 7,292,926 B2 | 11/2007 | Schmidt et al. |
| 7,302,937 B2 | 12/2007 | Ma et al. |
| 7,321,834 B2 | 1/2008 | Chu et al. |
| 7,323,036 B2 | 1/2008 | Boyden et al. |
| 7,328,577 B2 | 2/2008 | Stewart et al. |

(56) References Cited

U.S. PATENT DOCUMENTS

| | | |
|---|---|---|
| 7,337,022 B2 | 2/2008 | Wojsznis et al. |
| 7,349,776 B2 | 3/2008 | Spillane et al. |
| 7,357,125 B2 | 4/2008 | Kolavennu |
| 7,375,374 B2 | 5/2008 | Chen et al. |
| 7,376,471 B2 | 5/2008 | Das et al. |
| 7,383,118 B2 | 5/2008 | Imai et al. |
| 7,380,547 B1 | 6/2008 | Ruiz |
| 7,389,773 B2 | 6/2008 | Stewart et al. |
| 7,392,129 B2 | 6/2008 | Hill et al. |
| 7,397,363 B2 | 7/2008 | Joao |
| 7,398,082 B2 | 7/2008 | Schwinke et al. |
| 7,398,149 B2 | 7/2008 | Ueno et al. |
| 7,400,967 B2 | 7/2008 | Ueno et al. |
| 7,413,583 B2 | 8/2008 | Langer et al. |
| 7,415,389 B2 | 8/2008 | Stewart et al. |
| 7,418,372 B2 | 8/2008 | Nishira et al. |
| 7,430,854 B2 | 10/2008 | Yasui et al. |
| 7,433,743 B2 | 10/2008 | Pistikopoulos et al. |
| 7,444,191 B2 | 10/2008 | Caldwell et al. |
| 7,444,193 B2 | 10/2008 | Cutler |
| 7,447,554 B2 | 11/2008 | Cutler |
| 7,467,614 B2 | 12/2008 | Stewart et al. |
| 7,469,177 B2 | 12/2008 | Samad et al. |
| 7,474,953 B2 | 1/2009 | Hulser et al. |
| 7,493,236 B1 | 2/2009 | Mock et al. |
| 7,515,975 B2 | 4/2009 | Stewart |
| 7,522,963 B2 | 4/2009 | Boyden et al. |
| 7,536,232 B2 | 5/2009 | Boyden et al. |
| 7,542,842 B2 | 6/2009 | Hill et al. |
| 7,577,483 B2 | 8/2009 | Fan et al. |
| 7,587,253 B2 | 9/2009 | Rawlings et al. |
| 7,591,135 B2 | 9/2009 | Stewart |
| 7,599,749 B2 | 10/2009 | Sayyarrodsari et al. |
| 7,599,750 B2 | 10/2009 | Piche |
| 7,603,226 B2 | 10/2009 | Henein |
| 7,627,843 B2 | 12/2009 | Dozorets et al. |
| 7,630,868 B2 | 12/2009 | Turner et al. |
| 7,634,323 B2 | 12/2009 | Vermillion et al. |
| 7,634,417 B2 | 12/2009 | Boyden et al. |
| 7,650,780 B2 | 1/2010 | Hall |
| 7,668,704 B2 | 2/2010 | Perchanok et al. |
| 7,676,318 B2 | 3/2010 | Allain |
| 7,698,004 B2 | 4/2010 | Boyden et al. |
| 7,702,519 B2 | 4/2010 | Boyden et al. |
| 7,712,139 B2 | 5/2010 | Westendorf et al. |
| 7,721,030 B2 | 5/2010 | Fuehrer et al. |
| 7,725,199 B2 | 5/2010 | Brackney |
| 7,734,291 B2 | 6/2010 | Mazzara, Jr. |
| 7,743,606 B2 | 6/2010 | Havlena et al. |
| 7,748,217 B2 | 7/2010 | Muller |
| 7,752,840 B2 | 7/2010 | Stewart |
| 7,765,792 B2 | 8/2010 | Rhodes et al. |
| 7,779,680 B2 | 8/2010 | Sasaki et al. |
| 7,793,489 B2 | 9/2010 | Wang et al. |
| 7,798,938 B2 | 9/2010 | Matsubara et al. |
| 7,808,371 B2 | 10/2010 | Blanchet et al. |
| 7,826,909 B2 | 11/2010 | Attarwala |
| 7,831,318 B2 | 11/2010 | Bartee et al. |
| 7,840,287 B2 | 11/2010 | Wojsznis et al. |
| 7,844,351 B2 | 11/2010 | Piche |
| 7,844,352 B2 | 11/2010 | Youzis et al. |
| 7,846,299 B2 | 12/2010 | Backstrom et al. |
| 7,850,104 B2 | 12/2010 | Havlena et al. |
| 7,856,966 B2 | 12/2010 | Saitoh |
| 7,860,586 B2 | 12/2010 | Boyden et al. |
| 7,861,518 B2 | 1/2011 | Federle |
| 7,862,771 B2 | 1/2011 | Boyden et al. |
| 7,877,239 B2 | 1/2011 | Grichnik et al. |
| 7,878,178 B2 | 2/2011 | Stewart et al. |
| 7,891,669 B2 | 2/2011 | Araujo et al. |
| 7,904,280 B2 | 3/2011 | Wood |
| 7,905,103 B2 | 3/2011 | Larsen et al. |
| 7,907,769 B2 | 3/2011 | Sammak et al. |
| 7,925,399 B2 | 4/2011 | Comeau |
| 7,930,044 B2 | 4/2011 | Attarwala |
| 7,933,849 B2 | 4/2011 | Bartee et al. |
| 7,958,730 B2 | 6/2011 | Stewart |
| 7,987,145 B2 | 7/2011 | Baramov |
| 7,996,140 B2 | 8/2011 | Stewart et al. |
| 8,001,767 B2 | 8/2011 | Kakuya et al. |
| 8,019,911 B2 | 9/2011 | Dressier et al. |
| 8,025,167 B2 | 9/2011 | Schneider et al. |
| 8,032,235 B2 | 10/2011 | Sayyar-Rodsari |
| 8,046,089 B2 | 10/2011 | Renfro et al. |
| 8,060,290 B2 | 11/2011 | Stewart et al. |
| 8,078,291 B2 | 12/2011 | Pekar et al. |
| 8,109,255 B2 | 2/2012 | Stewart et al. |
| 8,121,818 B2 | 2/2012 | Gorinevsky |
| 8,145,329 B2 | 3/2012 | Pekar et al. |
| 8,209,963 B2 | 7/2012 | Kesse et al. |
| 8,229,163 B2 | 7/2012 | Coleman et al. |
| 8,265,854 B2 | 9/2012 | Stewart et al. |
| 8,281,572 B2 | 10/2012 | Chi et al. |
| 8,311,653 B2 | 11/2012 | Zhan et al. |
| 8,312,860 B2 | 11/2012 | Yun et al. |
| 8,316,235 B2 | 11/2012 | Boehl et al. |
| 8,360,040 B2 | 1/2013 | Stewart et al. |
| 8,370,052 B2 | 2/2013 | Lin et al. |
| 8,379,267 B2 | 2/2013 | Mestha et al. |
| 8,396,644 B2 | 3/2013 | Kabashima et al. |
| 8,402,268 B2 | 3/2013 | Dierickx |
| 8,453,431 B2 | 6/2013 | Wang et al. |
| 8,473,079 B2 | 6/2013 | Havlena |
| 8,478,506 B2 | 7/2013 | Grichnik et al. |
| RE44,452 E | 8/2013 | Stewart et al. |
| 8,504,175 B2 | 8/2013 | Pekar et al. |
| 8,505,278 B2 | 8/2013 | Farrell et al. |
| 8,543,170 B2 | 9/2013 | Mazzara, Jr. et al. |
| 8,555,613 B2 | 10/2013 | Wang et al. |
| 8,596,045 B2 | 12/2013 | Tuomivaara et al. |
| 8,620,461 B2 | 12/2013 | Kihas |
| 8,639,925 B2 | 1/2014 | Schuetze |
| 8,649,884 B2 | 2/2014 | MacArthur et al. |
| 8,649,961 B2 | 2/2014 | Hawkins et al. |
| 8,667,288 B2 | 3/2014 | Yavuz |
| 8,694,197 B2 | 4/2014 | Rajagopalan et al. |
| 8,700,291 B2 | 4/2014 | Hermann |
| 8,751,241 B2 | 6/2014 | Oesterling et al. |
| 8,762,026 B2 | 6/2014 | Wolfe et al. |
| 8,763,377 B2 | 7/2014 | Yacoub |
| 8,768,996 B2 | 7/2014 | Shokrollahi et al. |
| 8,813,690 B2 | 8/2014 | Kumar et al. |
| 8,867,746 B2 | 10/2014 | Ceskutti et al. |
| 8,892,221 B2 | 11/2014 | Kram et al. |
| 8,899,018 B2 | 12/2014 | Frazier et al. |
| 8,904,760 B2 | 12/2014 | Tai |
| 8,983,069 B2 | 3/2015 | Merchan et al. |
| 9,100,193 B2 | 8/2015 | Newsome et al. |
| 9,141,996 B2 | 9/2015 | Christensen et al. |
| 9,170,573 B2 | 10/2015 | Kihas |
| 9,175,595 B2 | 11/2015 | Ceynow et al. |
| 9,223,301 B2 | 12/2015 | Stewart et al. |
| 9,253,200 B2 | 2/2016 | Schwarz et al. |
| 9,325,494 B2 | 4/2016 | Boehl |
| 9,367,701 B2 | 6/2016 | Merchan et al. |
| 9,367,968 B2 | 6/2016 | Giraud et al. |
| 9,483,881 B2 | 11/2016 | Comeau et al. |
| 9,560,071 B2 | 1/2017 | Ruvio et al. |
| 9,779,742 B2 | 10/2017 | Newsome, Jr. |
| 2002/0112469 A1 | 8/2002 | Kanazawa et al. |
| 2002/0116104 A1 | 8/2002 | Kawashima et al. |
| 2003/0089102 A1 | 5/2003 | Colignon et al. |
| 2003/0150961 A1 | 8/2003 | Boelitz et al. |
| 2004/0006973 A1 | 1/2004 | Makki et al. |
| 2004/0034460 A1 | 2/2004 | Folkerts et al. |
| 2004/0086185 A1 | 5/2004 | Sun |
| 2004/0117766 A1 | 6/2004 | Mehta et al. |
| 2004/0118107 A1 | 6/2004 | Ament |
| 2004/0144082 A1 | 7/2004 | Mianzo et al. |
| 2004/0165781 A1 | 8/2004 | Sun |
| 2004/0199481 A1 | 10/2004 | Hartman et al. |
| 2004/0221889 A1 | 11/2004 | Dreyer et al. |
| 2004/0226287 A1 | 11/2004 | Edgar et al. |
| 2005/0209714 A1 | 2/2005 | Rawlings et al. |

(56) References Cited

U.S. PATENT DOCUMENTS

| | | |
|---|---|---|
| 2005/0107895 A1 | 5/2005 | Pistikopoulos et al. |
| 2005/0143952 A1 | 6/2005 | Tomoyasu et al. |
| 2005/0171667 A1 | 8/2005 | Morita |
| 2005/0187643 A1 | 8/2005 | Sayyar-Rodsari et al. |
| 2005/0193739 A1 | 9/2005 | Brunell et al. |
| 2005/0210868 A1 | 9/2005 | Funabashi |
| 2006/0047607 A1 | 3/2006 | Boyden et al. |
| 2006/0111881 A1 | 5/2006 | Jackson |
| 2006/0137347 A1 | 6/2006 | Stewart et al. |
| 2006/0168945 A1 | 8/2006 | Samad et al. |
| 2006/0185626 A1 | 8/2006 | Allen et al. |
| 2006/0212140 A1 | 9/2006 | Brackney |
| 2006/0265203 A1 | 11/2006 | Jenny et al. |
| 2006/0282178 A1 | 12/2006 | Das et al. |
| 2007/0101977 A1 | 5/2007 | Stewart |
| 2007/0142936 A1 | 6/2007 | Denison et al. |
| 2007/0144149 A1 | 6/2007 | Kolavennu et al. |
| 2007/0156259 A1 | 7/2007 | Baramov et al. |
| 2007/0240213 A1 | 10/2007 | Karam et al. |
| 2007/0261648 A1 | 11/2007 | Reckels et al. |
| 2007/0275471 A1 | 11/2007 | Coward |
| 2008/0010973 A1 | 1/2008 | Gimbres |
| 2008/0071395 A1 | 3/2008 | Pachner |
| 2008/0097625 A1 | 4/2008 | Vouzis et al. |
| 2008/0103747 A1 | 5/2008 | Macharia et al. |
| 2008/0103748 A1 | 5/2008 | Axelrud et al. |
| 2008/0104003 A1 | 5/2008 | Macharia et al. |
| 2008/0109100 A1 | 5/2008 | Macharia et al. |
| 2008/0125875 A1 | 5/2008 | Stewart et al. |
| 2008/0132178 A1 | 6/2008 | Chatterjee et al. |
| 2008/0183311 A1 | 7/2008 | MacArthur et al. |
| 2008/0208778 A1 | 8/2008 | Sayyar-Rodsari et al. |
| 2008/0244449 A1 | 10/2008 | Morrison et al. |
| 2008/0264036 A1 | 10/2008 | Bellovary |
| 2008/0289605 A1 | 11/2008 | Ito |
| 2009/0005889 A1 | 1/2009 | Sayyar-Rodsari |
| 2009/0008351 A1 | 1/2009 | Schneider et al. |
| 2009/0043546 A1 | 2/2009 | Srinivasan et al. |
| 2009/0087029 A1 | 4/2009 | Coleman et al. |
| 2009/0131216 A1 | 5/2009 | Matsubara et al. |
| 2009/0172416 A1 | 7/2009 | Bosch et al. |
| 2009/0182518 A1 | 7/2009 | Chu et al. |
| 2009/0198350 A1 | 8/2009 | Thiele |
| 2009/0204233 A1 | 8/2009 | Zhan et al. |
| 2009/0240480 A1 | 9/2009 | Baramov |
| 2009/0254202 A1 | 10/2009 | Pekar et al. |
| 2009/0287320 A1 | 11/2009 | MacGregor et al. |
| 2009/0312998 A1 | 12/2009 | Berckmans et al. |
| 2010/0017094 A1 | 1/2010 | Stewart et al. |
| 2010/0038158 A1 | 2/2010 | Whitney et al. |
| 2010/0050607 A1 | 3/2010 | He et al. |
| 2010/0122523 A1 | 5/2010 | Vosz |
| 2010/0126481 A1 | 5/2010 | Will et al. |
| 2010/0204808 A1 | 8/2010 | Thiele |
| 2010/0268353 A1 | 10/2010 | Crisalle et al. |
| 2010/0300069 A1 | 12/2010 | Hermann et al. |
| 2010/0300070 A1 | 12/2010 | He et al. |
| 2010/0305719 A1 | 12/2010 | Pekar et al. |
| 2010/0327090 A1 | 12/2010 | Havlena et al. |
| 2011/0006025 A1 | 1/2011 | Schneider et al. |
| 2011/0010073 A1 | 1/2011 | Stewart et al. |
| 2011/0029235 A1 | 2/2011 | Berry |
| 2011/0046752 A1 | 2/2011 | Piche |
| 2011/0056265 A1 | 3/2011 | Yacoub |
| 2011/0060424 A1 | 3/2011 | Havlena |
| 2011/0066308 A1 | 3/2011 | Yang et al. |
| 2011/0071653 A1 | 3/2011 | Kihas |
| 2011/0087420 A1 | 4/2011 | Stewart et al. |
| 2011/0104015 A1 | 5/2011 | Boyden et al. |
| 2011/0125293 A1 | 5/2011 | Havlena |
| 2011/0125295 A1 | 5/2011 | Bednasch et al. |
| 2011/0131017 A1 | 6/2011 | Cheng et al. |
| 2011/0167025 A1 | 7/2011 | Danai et al. |
| 2011/0173315 A1 | 7/2011 | Aguren |
| 2011/0257789 A1 | 10/2011 | Stewart et al. |
| 2011/0264353 A1 | 10/2011 | Atkinson et al. |
| 2011/0270505 A1 | 11/2011 | Chaturvedi et al. |
| 2011/0301723 A1 | 12/2011 | Pekar et al. |
| 2012/0024089 A1 | 2/2012 | Couey et al. |
| 2012/0109620 A1 | 5/2012 | Gaikwad et al. |
| 2012/0174187 A1 | 7/2012 | Argon et al. |
| 2013/0024069 A1 | 1/2013 | Wang et al. |
| 2013/0030554 A1 | 1/2013 | Macarthur et al. |
| 2013/0064717 A1 | 3/2013 | Masaki et al. |
| 2013/0067894 A1 | 3/2013 | Stewart et al. |
| 2013/0111878 A1 | 5/2013 | Pachner et al. |
| 2013/0111905 A1 | 5/2013 | Pekar et al. |
| 2013/0131954 A1 | 5/2013 | Yu et al. |
| 2013/0131956 A1 | 5/2013 | Thibault et al. |
| 2013/0131967 A1 | 5/2013 | Yu et al. |
| 2013/0158834 A1 | 6/2013 | Wagner et al. |
| 2013/0204403 A1 | 8/2013 | Zheng et al. |
| 2013/0242706 A1 | 9/2013 | Newsome, Jr. |
| 2013/0326232 A1 | 12/2013 | Lewis et al. |
| 2013/0326630 A1 | 12/2013 | Argon |
| 2013/0338900 A1 | 12/2013 | Ardanese et al. |
| 2014/0032189 A1 | 1/2014 | Hehle et al. |
| 2014/0034460 A1 | 2/2014 | Chou |
| 2014/0171856 A1 | 6/2014 | McLaughlin et al. |
| 2014/0258736 A1 | 9/2014 | Merchan et al. |
| 2014/0270163 A1 | 9/2014 | Merchan |
| 2014/0316683 A1 | 10/2014 | Whitney et al. |
| 2014/0318216 A1 | 10/2014 | Singh |
| 2014/0343713 A1 | 11/2014 | Ziegler et al. |
| 2014/0358254 A1 | 12/2014 | Chu et al. |
| 2015/0121071 A1 | 4/2015 | Schwarz et al. |
| 2015/0275783 A1 | 10/2015 | Wong et al. |
| 2015/0321642 A1 | 11/2015 | Schwepp et al. |
| 2015/0324576 A1 | 11/2015 | Quirant et al. |
| 2015/0334093 A1 | 11/2015 | Mueller |
| 2015/0354877 A1 | 12/2015 | Burns et al. |
| 2016/0003180 A1 | 1/2016 | McNulty et al. |
| 2016/0043832 A1 | 2/2016 | Ahn et al. |
| 2016/0108732 A1 | 4/2016 | Huang et al. |
| 2016/0127357 A1 | 5/2016 | Zibuschka et al. |
| 2016/0216699 A1 | 7/2016 | Pekar et al. |
| 2016/0239593 A1 | 8/2016 | Pekar et al. |
| 2016/0259584 A1 | 9/2016 | Schlottmann et al. |
| 2016/0330204 A1 | 11/2016 | Baur et al. |
| 2016/0344705 A1 | 11/2016 | Stumpf et al. |
| 2016/0362838 A1 | 12/2016 | Badwe et al. |
| 2016/0365977 A1 | 12/2016 | Boutros et al. |
| 2017/0031332 A1 | 2/2017 | Santin |
| 2017/0048063 A1 | 2/2017 | Mueller |
| 2017/0126701 A1 | 5/2017 | Glas et al. |
| 2017/0211453 A1* | 7/2017 | Sappok .......... G01N 22/04 |
| 2017/0218860 A1 | 8/2017 | Pachner et al. |
| 2017/0300713 A1 | 10/2017 | Fan et al. |
| 2017/0306871 A1 | 10/2017 | Fuxman et al. |
| 2018/0137695 A1* | 5/2018 | Sappok .......... F01N 3/2066 |
| 2018/0202341 A1* | 7/2018 | Piper .......... F01N 3/2066 |
| 2018/0223756 A1* | 8/2018 | Benson .......... F01N 9/00 |

FOREIGN PATENT DOCUMENTS

| | | |
|---|---|---|
| DE | 19628796 | 10/1997 |
| DE | 10219832 | 11/2002 |
| DE | 102009016509 | 10/2010 |
| DE | 102011103346 A1 | 8/2012 |
| EP | 0301527 | 2/1989 |
| EP | 0950803 | 4/1999 |
| EP | 0877309 | 6/2000 |
| EP | 1134368 | 3/2001 |
| EP | 1180583 | 2/2002 |
| EP | 1221544 | 7/2002 |
| EP | 1225490 | 7/2002 |
| EP | 1245811 | 10/2002 |
| EP | 1273337 | 1/2003 |
| EP | 1420153 A2 | 5/2004 |
| EP | 1447727 A2 | 8/2004 |
| EP | 1498791 A1 | 1/2005 |
| EP | 1425642 | 11/2005 |
| EP | 1686251 | 8/2006 |
| EP | 1399784 | 10/2007 |

(56) References Cited

FOREIGN PATENT DOCUMENTS

| | | |
|---|---|---|
| EP | 2107439 | 10/2009 |
| EP | 2146258 | 1/2010 |
| EP | 1794339 | 7/2011 |
| EP | 1529941 | 11/2011 |
| EP | 2543845 A1 | 1/2013 |
| EP | 2551480 A1 | 1/2013 |
| EP | 2589779 A2 | 5/2013 |
| EP | 2617975 | 7/2013 |
| EP | 2267559 | 1/2014 |
| EP | 2919079 | 9/2015 |
| JP | 59190443 | 10/1984 |
| JP | 2010282618 | 12/2010 |
| WO | 0144629 A2 | 6/2001 |
| WO | 0169056 A1 | 9/2001 |
| WO | WO 02/32552 | 4/2002 |
| WO | WO 02/097540 | 12/2002 |
| WO | WO 02/101208 | 12/2002 |
| WO | WO 03/023538 | 3/2003 |
| WO | 03048533 A1 | 6/2003 |
| WO | WO 2003/048533 | 6/2003 |
| WO | WO 03/065135 | 8/2003 |
| WO | WO 03/078816 | 9/2003 |
| WO | 03102394 A1 | 12/2003 |
| WO | WO 2004/027230 | 4/2004 |
| WO | WO 2006/021437 | 3/2006 |
| WO | WO 2007/078907 | 7/2007 |
| WO | WO 2008/033800 | 3/2008 |
| WO | WO 2008/115911 | 9/2008 |
| WO | WO 2012/076838 | 6/2012 |
| WO | WO 2013/119665 | 8/2013 |
| WO | WO 2014/165439 | 10/2014 |
| WO | WO 2016/053194 | 4/2016 |

OTHER PUBLICATIONS

"Chapter 14: Pollutant Formation," Fluent Manual, Release 15.0, Chapter 14, pp. 313-345, prior to Jan. 29, 2016.
"Chapter 21, Modeling Pollutant Formation," Fluent Manual, Release 12.0, Chapter 21, pp. 21-1—21-54, Jan. 30, 2009.
"J1979 E/E Diagnostic Test Modules," Proposed Regulation, Vehicle E.E. System Diagnostic Standards Committee, 1 page, Sep. 28, 2010.
"MicroZed Zynq Evaluation and Development and System on Module, Hardware User Guide," Avnet Electronics Marketing, Version 1.6, Jan. 22, 2015.
Actron, "Elite AutoScanner Kit—Enhanced OBD I & II Scan Tool, OBD 1300," Downloaded from https://actron.com/content/elite-autoscanner-kit-enhanced-obd-i-and-obd-ii-scan-tool?utm_ . . . , 5 pages, printed Sep. 27, 2016.
Andersson et al., "A Predictive Real Time NOx Model for Conventional and Partially Premixed Diesel Combustion," SAE International 2006-01-3329, 10 pages, 2006.
Andersson et al., "A Real Time NOx Model for Conventional and Partially Premixed Diesel Combustion," SAE Technical Paper Series 2006-01-0195, 2006 SAE World Congress, 13 pages, Apr. 3-6, 2006.
Andersson et al., "Fast Physical NOx Prediction in Diesel Engines, The Diesel Engine: The Low CO2 and Emissions Reduction Challenge," Conference Proceedings, Lyon, 2006. Unable to Obtain a Copy of This Reference.
Arregle et al., "On Board NOx Prediction in Diesel Engines: A Physical Approach," Automotive Model Predictive Control, Models Methods and Applications, Chapter 2, 14 pages, 2010.
Asprion, "Optimal Control of Diesel Engines," PHD Thesis, Diss ETH No. 21593, 436 pages, 2013.
Assanis et al., "A Predictive Ignition Delay Correlation Under Steady-State and Transient Operation of a Direct njection Diesel Engine," ASME, Journal of Engineering for Gas Turbines and Power, vol. 125, pp. 450-457, Apr. 2003.
Bako et al., "A Recursive Identification Algorithm for Switched Linear/Affine Models," Nonlinear Analysis: Hybrid Systems, vol. 5, pp. 242-253, 2011.

Barba et al., "A Phenomenological Combustion Model for Heat Release Rate Prediction in High-Speed DI Diesel Engines with Common Rail Injection," SAE Technical Paper Series 2000-01-2933, International Fall Fuels and Lubricants Meeting Exposition, 15 pages, Oct. 16-19, 2000.
Blanco-Rodriguez, "Modelling and Observation of Exhaust Gas Concentrations for Diesel Engine Control," Phd Dissertation, 242 pages, Sep. 2013.
Blue Streak Electronics Inc., "Ford Modules," 1 page, May 12, 2010.
Boum et al., "Advanced Compressor Engine Controls to Enhance Operation, Reliability and Integrity," Southwest Research Institute, DOE Award No. DE-FC26-03NT41859, SwRI Project No. 03.10198, 60 pages, Mar. 2004.
Charalampidis et al., "Computationally Efficient Kalman Filtering for a Class of Nonlinear Systems," IEEE Transactions an Automatic Control, vol. 56, No. 3, pp. 483-491, Mar. 2011.
Chew, "Sensor Validation Scheme with Virtual NOx Sensing for Heavy Duty Diesel Engines," Master's Thesis, 144 pages, 2007.
The Extended European Search Report for EP Application No. 15155295.7-1606, dated Aug. 4, 2015.
The Extended European Search Report for EP Application No. 15179435.1, dated Apr. 1, 2016.
Desantes et al., "Development of NOx Fast Estimate Using NOx Sensor," EAEC 2011 Congress, 2011. Unable to Obtain a Copy of This Reference.
Ding, "Characterising Combustion in Diesel Engines, Using Parameterised Finite Stage Cylinder Process Models," 281 pages, Dec. 21, 2011.
Docquier et al., "Combustion Control and Sensors: a Review," Progress in Energy and Combustion Science, vol. 28, pp. 107-150, 2002.
Egnell, "Combustion Diagnostics by Means of Multizone Heat Release Analysis and NO Calculation," SAE Technical Paper Series 981424, International Spring Fuels and Lubricants Meeting and Exposition, 22 pages, May 4-6, 1998.
Ericson, "NOx Modelling of a Complete Diesel Engine/SCR System," Licentiate Thesis, 57 pages, 2007.
Finesso et al., "Estimation of the Engine-Out NO2/NOx Ration in a Euro VI Diesel Engine," SAE International 2013-01-0317, 15 pages, Apr. 8, 2013.
Fleming, "Overview of Automotive Sensors," IEEE Sensors Journal, vol. 1, No. 4, pp. 296-308, Dec. 2001.
Ford Motor Company, "2012 My OBD System Operation Summary for 6.7L Diesel Engines," 149 pages, Apr. 21, 2011.
Formentin et al., "NOx Estimation in Diesel Engines Via In-Cylinder Pressure Measurement," IEEE Transactions on Control Systems Technology, vol. 22, No. 1, pp. 396-403, Jan. 2014.
Galindo, "An On-Engine Method for Dynamic Characterisation of NOx Concentration Sensors," Experimental Thermal and Fluid Science, vol. 35, pp. 470-476, 2011.
Gamma Technologies, "Exhaust Aftertreatment with GT-Suite," 2 pages, Jul. 17, 2014.
Guardiola et al., "A Bias Correction Method for Fast Fuel-to-Air Ratio Estimation in Diesel Engines," Proceedings of the Institution of Mechanical Engineers, Part D: Journal of Automobile Engineering, vol. 227, No. 8, pp. 1099-1111, 2013.
Guardiola et al., "A Computationally Efficient Kalman Filter Based Estimator for Updating Look-Up Tables Applied to NOx Estimation in Diesel Engines," Control Engineering Practice, vol. 21, pp. 1455-1468.
Guzzella et al., "Introduction to Modeling and Control of Internal Combustion Engine Systems," 303 pages, 2004.
Hahlin, "Single Cylinder ICE Exhaust Optimization," Master's Thesis, retrieved from https://pure.Itu.se/portal/files/44015424/LTU-EX-2013-43970821.pdf, 50 pages, Feb. 1, 2014.
Hammacher Schlemmer, "The Windshield Heads Up Display," Catalog, p. 47, prior to Apr. 26, 2016.
Heywood, "Pollutant Formation and Control," Internal Combustion Engine Fundamentals, pp. 567-667, 1988.
Hirsch et al., "Dynamic Engine Emission Models," Automotive Model Predictive Control, Chapter 5, 18 pages, LNCIS 402, 2012.

(56) References Cited

OTHER PUBLICATIONS

Hirsch et al., "Grey-Box Control Oriented Emissions Models," The International Federation of Automatic Control (IFAC), Proceedings of the 17th World Congress, pp. 8514-8519, Jul. 6-11, 2008.
Hockerdal, "EKF-based Adaptation of Look-Up Tables with an Air Mass-Flow Sensor Application," Control Engineering Practice, vol. 19, 12 pages, 2011.
http://nexceris.com/news/nextech-materials/, "NEXTECH Materials is Now NEXCERIS," 7 pages, printed Oct. 4, 2016.
http://www.arb.ca.gov/msprog/obdprog/hdobdreg.htm, "Heavy-Duty OBD Regulations and Rulemaking," 8 pages, printed Oct. 4, 2016.
http://www.not2fast.wryday.com/turbo/glossary/turbo_glossary.shtml, "Not2Fast: Turbo Glossary," 22 pages, printed Oct. 1, 2004.
http://www.tai-cwv.com/sbl106.0.html, "Technical Overview-Advanced Control Solutions," 6 pages, printed Sep. 9, 2004.
https://www.dieselnet.com/standards/us/obd.php, "Emission Standards: USA: On-Board Diagnostics," 6 pages, printed Oct. 3, 2016.
https://www.en.wikipedia.org/wiki/Public-key_cryptography, "Public-Key Cryptography," 14 pages, printed Feb. 26, 2016.
Ishida et al., "An Analysis of the Added Water Effect on NO Formation in D.I. Diesel Engines," SAE Technical Paper Series 941691, International Off-Highway and Power-Plant Congress and Exposition, 13 pages, Sep. 12-14, 1994.
Ishida et al., "Prediction of NOx Reduction Rate Due to Port Water Injection in a DI Diesel Engine," SAE Technical Paper Series 972961, International Fall Fuels and Lubricants Meeting and Exposition, 13 pages, Oct. 13-16, 1997.
Jensen, "The 13 Monitors of an OBD System," http://www.oemoffhighway.com/article/1 0855512/the-13-monito . . . , 3 pages, printed Oct. 3, 2016.
Extended European Search Report for EP Application Serial No. 15155295.7 dated Aug. 4, 2015.
The Extended European Search Report for EP Application No. 17151521.6, dated Oct. 23, 2017.
The Extended European Search Report for EP Application No. 17163452.0, dated Sep. 26, 2017.
Greenberg, "Hackers Cut a Corvette's Brakes Via A Common Car Gadget," downloaded from https://www.wired.com2015/08/hackers-cut-corvettes-brakes-v . . . , 14 pages, Aug. 11, 2015, printed Dec. 11, 2017.
http://www.blackpoolcommunications.com/products/alarm-immo . . . , "OBD Security OBD Port Protection—Alarms & Immobilizers . . . ," 1 page, printed Jun. 5, 2017.
http://www.cnbc.com/2016/09/20/chinese-company-hacks-tesla-car-remotely.html, "Chinese Company Hacks Tesla Car Remotely," 3 pages, Sep. 20, 2016.
ISO, "ISO Document No. 13185-2:2015(E)," 3 pages, 2015.
Khair et al., "Emission Formation in Diesel Engines," Downloaded from https://www.dieselnet.com/tech/diesel_emiform.php, 33 pages, printed Oct. 14, 2016.
Kihas et al., "Chapter 14, Diesel Engine SCR Systems: Modeling Measurements and Control," Catalytic Reduction Technology (book), Part 1, Chapter 14, prior to Jan. 29, 2016.
Krause et al., "Effect of Inlet Air Humidity and Temperature on Diesel Exhaust Emissions," SAE International Automotive Engineering Congress, 8 pages, Jan. 8-12, 1973.
Lavoie et al., "Experimental and Theoretical Study of Nitric Oxide Formation in Internal Combustion Engines," Combustion Science and Technology, vol. 1, pp. 313-326, 1970.
Manchur et al., "Time Resolution Effects on Accuracy of Real-Time NOx Emissions Measurements," SAE Technical Paper Series 2005-01-0674, 2005 SAE World Congress, 19 pages, Apr. 11-14, 2005.
Mohammadpour et al., "A Survey on Diagnostics Methods for Automotive Engines," 2011 American Control Conference, pp. 985-990, Jun. 29, 2011-Jul. 1, 2011.
Moos, "Catalysts as Sensors—A Promising Novel Approach in Automotive Exhaust Gas Aftertreatment," http://www.mdpi.com/1424-8220/10/7/6773htm, 10 pages, Jul. 13, 2010.

Olsen, "Analysis and Simulation of the Rate of Heat Release (ROHR) in Diesel Engines," MSc-Assignment, 105 pages, Jun. 2013.
Payri et al., "Diesel NOx Modeling with a Reduction Mechanism for the Initial NOx Coming from EGR or Re-Entrained Burned Gases," 2008 World Congress, SAE Technical Paper Series 2008-01-1188, 13 pages, Apr. 14-17, 2008.
Payri et al., "Methodology for Design and Calibration of a Drift Compensation Method for Fuel-to-Air Ratio," SAE International 2012-01-0717, 13 pages, Apr. 16, 2012.
Pipho et al., "NO2 Formation in a Diesel Engine," SAE Technical Paper Series 910231, International Congress and Exposition, 15 pages, Feb. 25, 1991-Mar. 1, 1991.
Querel et al., "Control of an SCR System Using a Virtual NOx Sensor," 7th IFAC Symposium on Advances in Automotive Control, The International Federation of Automotive Control, pp. 9-14, Sep. 4-7, 2013.
Ricardo Software, "Powertrain Design at Your Fingertips," retrieved from http://www.ricardo.com/PageFiles/864/WaveFlyerA4_4PP.pdf, 2 pages, downloaded Jul. 27, 2015.
Santin et al., "Combined Gradient/Newton Projection Semi-Explicit QP Solver for Problems with Bound Constraints," 2 pages, prior to Jan. 29, 2016.
Schilling et al., "A Real-Time Model for the Prediction of the NOx Emissions in DI Diesel Engines," Proceedings of the 2006 IEEE International Conference on Control Applications, pp. 2042-2047, Oct. 4-7, 2006.
Schilling, "Model-Based Detection and Isolation of Faults in the Air and Fuel Paths of Common-Rail DI Diesel Engines Equipped with a Lambda and a Nitrogen Oxides Sensor," Doctor of Sciences Dissertation, 210 pages, 2008.
Shahzad et al., "Preconditioners for Inexact Interior Point Methods for Predictive Control," 2010 American Control Conference, pp. 5714-5719, Jun. 30, 2010-Jul. 2010.
Signer et al., "European Programme on Emissions, Fuels and Engine Technologies (EPEFE)—Heavy Duty Diesel Study," International Spring Fuels and Lubricants Meeting, SAE 961074, May 6-8, 1996.
Smith, "Demonstration of a Fast Response On-Board NOx Sensor for Heavy-Duty Diesel Vehicles," Technical report, Southwest Research Institute Engine and Vehicle Research Division SwRI Project No. 03-02256 Contract No. 98-302, 2000. Unable to Obtain a Copy of This Reference.
Stradling et al., "The Influene of Fuel Properties and Injection Timing on the Exhaust Emissions and Fuel Consumption of an Iveco Heavy-Duty Diesel Engine," International Spring Fuels and Lubricants Meeting, SAE 971635, May 5-8, 1997.
Traver et al., "A Neural Network-Based Virtual NOx Sensor for Diesel Engines," 7 pages, prior to Jan. 29, 2016.
Tschanz et al., "Cascaded Multivariable Control of the Combustion in Diesel Engines," The International Federation of Automatic Control (IFAC), 2012 Workshop on Engine and Powertrain Control, Simulation and Modeling, pp. 25-32, Oct. 23-25, 2012.
Tschanz et al., "Control of Diesel Engines Using NOx-Emission Feedback," International Journal of Engine Research, vol. 14, No. 1, pp. 45-56, 2013.
Tschanz et al., "Feedback Control of Particulate Matter and Nitrogen Oxide Emissions in Diesel Engines," Control Engineering Practice, vol. 21, pp. 1809-1820, 2013.
Turner, "Automotive Sensors, Sensor Technology Series," Momentum Press, Unable to Obtain the Entire Book, a Copy of the Front and Back Covers and Table of Contents are Provided, 2009.
Van Helden et al., "Optimization of Urea SCR deNOx Systems for HD Diesel Engines," SAE International 2004-01-0154, 13 pages, 2004.
VDO, "UniNOx-Sensor Specification," Continental Trading GmbH, 2 pages, Aug. 2007.
Vereschaga et al., "Piecewise Affine Modeling of NOx Emission Produced by a Diesel Engine," 2013 European Control Conference (ECC), pp. 2000-2005, Jul. 17-19, 2013.
Wahlstrom et al., "Modelling Diesel Engines with a Variable-Geometry Turbocharger and Exhaust Gas Recirculation by Optimization of Model Parameters for Capturing Non-Linear System

(56) References Cited

OTHER PUBLICATIONS

Dynamics," (Original Publication) Proceedings of the Institution of Mechanical Engineers, Part D, Journal of Automobile Engineering, vol. 225, No. 7, 28 pages, 2011.

Wang et al., "Sensing Exhaust NO2 Emissions Using the Mixed Potential Principal," SAE 2014-01-1487, 7 pages, Apr. 1, 2014.

Wilhelmsson et al., "A Fast Physical NOx Model Implemented on an Embedded System," Proceedings of the IFAC Workshop on Engine and Powertrain Control, Simulation and Modeling, pp. 207-215, Nov. 30, 2009-Dec. 2, 2009.

Wilhemsson et al., "A Physical Two-Zone NOx Model Intended for Embedded Implementation," SAE 2009-01-1509, 11 pages, 2009.

Winkler et al., "Incorporating Physical Knowledge About the Formation of Nitric Oxides into Evolutionary System dentification," Proceedings of the 20th European Modeling and Simulation Symposium (EMSS), 6 pages, 2008.

Winkler et al., "On-Line Modeling Based On Genetic Programming," 12 pages, International Journal on Intelligent Systems Technologies and Applications 2, 2007.

Winkler et al., "Using Genetic Programming in Nonlinear Model Identification," 99 pages, prior to Jan. 29, 2016.

Winkler et al., "Virtual Sensors for Emissions of a Diesel Engine Produced by Evolutionary System Identification," LNCS, vol. 5717, 8 pages, 2009.

Winkler, "Evolutionary System Identification—Modern Approaches and Practical Applications," Kepler Universitat Linz, Reihe C: Technik und Naturwissenschaften, Universitatsverlag Rudolf Trauner, 2009. Unable to Obtain a Copy of This Reference.

Wong, "CARB Heavy-Duty OBD Update," California Air Resources Board, SAE OBD TOPTEC, Downloaded from http://www.arb.ca.gov/msprog/obdprog/hdobdreg.htm, 72 pages, Sep. 15, 2005.

Yao et al., "The Use of Tunnel Concentration Profile Data to Determine the Ratio of NO2/NOx Directly Emitted from Vehicles," HAL Archives, 19 pages, 2005.

Zaman, "Lincoln Motor Company: Case study 2015 Lincoln MKC," Automotive Electronic Design Fundamentals, Chapter 6, 2015.

Zeldovich, "The Oxidation of Nitrogen in Combustion and Explosions," ACTA Physiochimica U.R.S.S., vol. XX1, No. 4, 53 pages, 1946.

Zhuiykov et al., "Development of Zirconia-Based Potentiometric NOx Sensors for Automotive and Energy Industries in the Early 21st Century: What Are the Prospects for Sensors?", Sensors and Actuators B, vol. 121, pp. 639-651, 2007.

Goodwin, "Researchers Hack A Corvette's Brakes Via Insurance Black Box," Downloaded from http://www.cnet.com/roadshow/news/researchers-hack-a-corvettes-brakes-via-insurance-black-box/, 2 pages, Aug. 2015.

Greenberg, "Hackers Remotely Kill A Jeep On The Highway—With Me In It," Downloaded from http://www.wired.com/2015/07/hackers-remotely-kill-jeep-highway/, 24 pages, Jul. 21, 2015.

"Model Predictive Control Toolbox Release Notes," The Mathworks, 24 pages, Oct. 2008.

"Model Predictive Control," Wikipedia, pp. 1-5, Jan. 22, 2009. http://en.wikipedia.org/w/index.php?title=Special:Book&bookcmd=download&collecton_id=641cd1b5da77cc22&writer=r1&return_to=Model predictive control, retrieved Nov. 20, 2012.

"MPC Implementation Methods for the Optimization of the Response of Control Valves to Reduce Variability," Advanced Application Note 002, Rev. A, 10 pages, 2007.

"SCR, 400-csi Coated Catalyst," Leading NOx Control Technologies Status Summary, 1 page prior to Feb. 2, 2005.

Advanced Petroleum-Based Fuels-Diesel Emissions Control (APBF-DEC) Project, "Quarterly Update," No. 7, 6 pages, Fall 2002.

Allanson, et al., "Optimizing the Low Temperature Performance and Regeneration Efficiency of the Continuously Regenerating Diesel Particulate Filter System," SAE Paper No. 2002-01-0428, 8 pages, Mar. 2002.

Amstuz, et al., "EGO Sensor Based Robust Output Control of EGR in Diesel Engines," IEEE TCST, vol. 3, No. 1, 12 pages, Mar. 1995.

Axehill et al., "A Dual Gradiant Projection Quadratic Programming Algorithm Tailored for Model Predictive Control," Proceedings of the 47th IEEE Conference on Decision and Control, Cancun Mexico, pp. 3057-3064, Dec. 9-11, 2008.

Axehill et al., "A Dual Gradient Projection Quadratic Programming Algorithm Tailored for Mixed Integer Predictive Control," Technical Report from Linkopings Universitet, Report No. Li-Th-ISY-R-2833, 58 pages, Jan. 31, 2008.

Baffi et al., "Non-Linear Model Based Predictive Control Through Dynamic Non-Linear Partial Least Squares," Trans IChemE, vol. 80, Part A, pp. 75-86, Jan. 2002.

Bemporad et al., "Model Predictive Control Toolbox 3, User's Guide," Matlab Mathworks, 282 pages, 2008.

Bemporad et al., "The Explicit Linear Quadratic Regulator for Constrained Systems," Automatica, 38, pp. 3-20, 2002.

Bemporad, "Model Predictive Control Based on Linear Programming—The Explicit Solution," IEEE Transactions on Automatic Control, vol. 47, No. 12, pp. 1974-1984, Dec. 2002.

Bemporad, "Model Predictive Control Design: New Trends and Tools," Proceedings of the 45th IEEE Conference on Decision & Control, pp. 6678-6683, Dec. 13-15, 2006.

Bemporad, et al., "Explicit Model Predictive Control," 1 page, prior to Feb. 2, 2005.

Bertsekas, "On the Goldstein-Levitin-Polyak Gradient Projection Method," IEEE Transactions on Automatic Control, vol. AC-21, No. 2, pp. 174-184, Apr. 1976.

Bertsekas, "Projected Newton Methods for Optimization Problems with Simple Constraints*," SIAM J. Control and Optimization, vol. 20, No. 2, pp. 221-246, Mar. 1982.

Borrelli et al., "An MPC/Hybrid System Approach to Traction Control," IEEE Transactions on Control Systems Technology, vol. 14, No. 3, pp. 541-553, May 2006.

Borrelli, "Constrained Optimal Control of Linear and Hybrid Systems," Lecture Notes in Control and Information Sciences, vol. 290, 2003.

Borrelli, "Discrete Time Constrained Optimal Control," A Dissertation Submitted to the Swiss Federal Institute of Technology (ETH) Zurich, Diss. ETH No. 14666, 232 pages, Oct. 9, 2002.

Catalytica Energy Systems, "Innovative NOx Reduction Solutions for Diesel Engines," 13 pages, 3rd Quarter, 2003.

Chatterjee, et al. "Catalytic Emission Control for Heavy Duty Diesel Engines," JM, 46 pages, prior to Feb. 2, 2005.

European Search Report for EP Application No. 12191156.4-1603 dated Feb. 9, 2015.

European Search Report for EP Application No. EP 10175270.7-2302419 dated Jan. 16, 2013.

European Search Report for EP Application No. EP 15152957.5-1807 dated Feb. 10, 2015.

Search Report for Corresponding EP Application No. 11167549.2 dated Nov. 27, 2012.

U.S. Appl. No. 15/005,406, filed Jan. 25, 2016.

U.S. Appl. No. 15/011,445, filed Jan. 29, 2016.

De Oliveira, "Constraint Handling and Stability Properties of Model Predictive Control," Carnegie Institute of Technology, Department of Chemical Engineering, Paper 197, 64 pages, Jan. 1, 1993.

De Schutter et al., "Model Predictive Control for Max-Min-Plus-Scaling Systems," Proceedings of the 2001 American Control Conference, Arlington, Va, pp. 319-324, Jun. 2001.

Delphi, Delphi Diesel NOx Trap (DNT), 3 pages, Feb. 2004.

Diehl et al., "Efficient Numerical Methods for Nonlinear MPC and Moving Horizon Estimation," Int. Workshop on Assessment and Future Directions of NMPC, 24 pages, Pavia, Italy, Sep. 5-9, 2008.

Dunbar, "Model Predictive Control: Extension to Coordinated Multi-Vehicle Formations and Real-Time Implementation," CDS Technical Report 01-016, 64 pages, Dec. 7, 2001.

GM "Advanced Diesel Technology and Emissions," powertrain technologies—engines, 2 pages, prior to Feb. 2, 2005.

Guerreiro et al., "Trajectory Tracking Nonlinear Model Predictive Control for Autonomous Surface Craft," Proceedings of the European Control Conference, Budapest, Hungary, 6 pages, Aug. 2009.

Guzzella, et al., "Control of Diesel Engines," IEEE Control Systems Magazine, pp. 53-71, Oct. 1998.

(56) References Cited

OTHER PUBLICATIONS

Havelena, "Componentized Architecture for Advanced Process Management," Honeywell International, 42 pages, 2004.
Hiranuma, et al., "Development of DPF System for Commercial Vehicle—Basic Characteristic and Active Regeneration Performance," SAE Paper No. 2003-01-3182, Mar. 2003.
Honeywell, "Profit Optimizer A Distributed Quadratic Program (DQP) Concepts Reference," 48 pages, prior to Feb. 2, 2005.
http://www.tai-cwv.com/sb1106.0.html, "Technical Overview—Advanced Control Solutions," 6 pages, printed Sep. 9, 2004.
Johansen et al., "Hardware Architecture Design for Explicit Model Predictive Control," Proceedings of ACC, 6 pages, 2006.
Johansen et al., "Hardware Synthesis of Explicit Model Predictive Controllers," IEEE Transactions on Control Systems Technology, vol. 15, No. 1, Jan. 2007.
Jonsson, "Fuel Optimized Predictive Following in Low Speed Conditions," Master's Thesis, 46 pages, Jun. 28, 2003.
Kelly, et al., "Reducing Soot Emissions from Diesel Engines Using One Atmosphere Uniform Glow Discharge Plasma," SAE Paper No. 2003-01-1183, Mar. 2003.
Keulen et al., "Predictive Cruise Control in Hybrid Electric Vehicles", May 2009, World Electric Journal, vol. 3, ISSN 2032-6653.
Kolmanovsky, et al., "Issues in Modeling and Control of Intake Flow in Variable Geometry Turbocharged Engines", 18th IFIP Conf. System Modeling and Optimization, pp. 436-445, Jul. 1997.
Kulhavy, et al. "Emerging Technologies for Enterprise Optimization in the Process Industries," Honeywell, 12 pages, Dec. 2000.
Locker, et al., "Diesel Particulate Filter Operational Characterization," Corning Incorporated, 10 pages, prior to Feb. 2, 2005.
Lu, "Challenging Control Problems and Engineering Technologies in Enterprise Optimization," Honeywell Hi-Spec Solutions, 30 pages, Jun. 4-6, 2001.
Maciejowski, "Predictive Control with Constraints," Prentice Hall, Pearson Education Limited, 4 pages, 2002.
Mariethoz et al., "Sensorless Explicit Model Predictive Control of the DC-DC Buck Converter with Inductor Current Limitation," IEEE Applied Power Electronics Conference and Exposition, pp. 1710-1715, 2008.
Marjanovic, "Towards a Simplified Infinite Horizon Model Predictive Controller," 6 pages, Proceedings of the $5^{th}$ Asian Control Conference, 6 pages, Jul. 20-23, 2004.
Mayne et al., "Constrained Model Predictive Control: Stability and Optimality," Automatica, vol. 36, pp. 789-814, 2000.
Mehta, "The Application of Model Predictive Control to Active Automotive Suspensions," 56 pages, May 17, 1996.
Moore, "Living with Cooled-EGR Engines," Prevention Illustrated, 3 pages, Oct. 3, 2004.
Murayama et al., "Speed Control of Vehicles with Variable Valve Lift Engine by Nonlinear MPC," ICROS-SICE International Joint Conference, pp. 4128-4133, 2009.
National Renewable Energy Laboratory (NREL), "Diesel Emissions Control- Sulfur Effects Project (DECSE) Summary of Reports," U.S. Department of Energy, 19 pages, Feb. 2002.
Ortner et al., "MPC for a Diesel Engine Air Path Using an Explicit Approach for Constraint Systems," Proceedings of the 2006 IEEE Conference on Control Applications, Munich Germany, pp. 2760-2765, Oct. 4-6, 2006.
Ortner et al., "Predictive Control of a Diesel Engine Air Path," IEEE Transactions on Control Systems Technology, vol. 15, No. 3, pp. 449-456, May 2007.
Pannocchia et al., "Combined Design of Disturbance Model and Observer for Offset-Free Model Predictive Control," IEEE Transactions on Automatic Control, vol. 52, No. 6, 6 pages, 2007.
Patrinos et al., "A Global Piecewise Smooth Newton Method for Fast Large-Scale Model Predictive Control," Tech Report TR2010-02, National Technical University of Athens, 23 pages, 2010.
Qin et al., "A Survey of Industrial Model Predictive Control Technology," Control Engineering Practice, 11, pp. 733-764, 2003.
Rajamani, "Data-based Techniques to Improve State Estimation in Model Predictive Control," Ph.D. Dissertation, 257 pages, 2007.
Rawlings, "Tutorial Overview of Model Predictive Control," IEEE Control Systems Magazine, pp. 38-52, Jun. 2000.
Salvat, et al., "Passenger Car Serial Application of a Particulate Filter System on a Common Rail Direct Injection Engine," SAE Paper No. 2000-01-0473, 14 pages, Feb. 2000.
Schauffele et al., "Automotive Software Engineering Principles, Processes, Methods, and Tools," SAE International, 10 pages, 2005.
Shamma, et al. "Approximate Set-Valued Observers for Nonlinear Systems," IEEE Transactions on Automatic Control, vol. 42, No. 5, May 1997.
Soltis, "Current Status of NOx Sensor Development," Workshop on Sensor Needs and Requirements for PEM Fuel Cell Systems and Direct-Injection Engines, 9 pages, Jan. 25-26, 2000.
Stefanopoulou, et al., "Control of Variable Geometry Turbocharged Diesel Engines for Reduced Emissions," IEEE Transactions on Control Systems Technology, vol. 8, No. 4, pp. 733-745, Jul. 2000.
Stewart et al., "A Model Predictive Control Framework for Industrial Turbodiesel Engine Control," Proceedings of the $47^{th}$ IEEE Conference on Decision and Control, 8 pages, 2008.
Stewart et al., "A Modular Model Predictive Controller for Turbodiesel Problems," First Workshop on Automotive Model Predictive Control, Schloss Muhldorf, Feldkirchen, Johannes Kepler University, Linz, 3 pages, 2009.
Storset, et al., "Air Charge Estimation for Turbocharged Diesel Engines," vol. 1 Proceedings of the American Control Conference, 8 pages, Jun. 28-30, 2000.
Takacs et al., "Newton-Raphson Based Efficient Model Predictive Control Applied on Active Vibrating Structures," Proceeding of the European Control Conference 2009, Budapest, Hungary, pp. 2845-2850, Aug. 23-26, 2009.
The MathWorks, "Model-Based Calibration Toolbox 2.1 Calibrate complex powertrain systems," 4 pages, prior to Feb. 2, 2005.
The MathWorks, "Model-Based Calibration Toolbox 2.1.2," 2 pages, prior to Feb. 2, 2005.
Theiss, "Advanced Reciprocating Engine System (ARES) Activities at the Oak Ridge National Lab (ORNL), Oak Ridge National Laboratory," U.S. Department of Energy, 13 pages, Apr. 14, 2004.
Tondel et al., "An Algorithm for Multi-Parametric Quadratic Programming and Explicit MPC Solutions," Automatica, 39, pp. 489-497, 2003.
Van Basshuysen et al., "Lexikon Motorentechnik," (Dictionary of Automotive Technology) published by Vieweg Verlag, Wiesbaden 039936, p. 518, 2004. (English Translation).
Van Den Boom et al., "MPC for Max-Plus-Linear Systems: Closed-Loop Behavior and Tuning," Proceedings of the 2001 American Control Conference, Arlington, Va, pp. 325-330, Jun. 2001.
Van Keulen et al., "Predictive Cruise Control in Hybrid Electric Vehicles," World Electric Vehicle Journal vol. 3, ISSN 2032-6653, pp. 1-11, 2009.
Wang et al., "Fast Model Predictive Control Using Online Optimization," Proceedings of the $17^{th}$ World Congress, the International Federation of Automatic Control, Seoul, Korea, pp. 6974-6979, Jul. 6-11, 2008.
Wang et al., "PSO-Based Model Predictive Control for Nonlinear Processes," Advances in Natural Computation, Lecture Notes in Computer Science, vol. 3611/2005, 8 pages, 2005.
Wright, "Applying New Optimization Algorithms to Model Predictive Control," 5th International Conference on Chemical Process Control, 10 pages, 1997.
Zavala et al., "The Advance-Step NMPC Controller: Optimality, Stability, and Robustness," Automatica, vol. 45, pp. 86-93, 2009.
Zeilinger et al., "Real-Time MPC—Stability Through Robust MPC Design," Joint $48^{th}$ IEEE Conference on Decision and Control and $28^{th}$ Chinese Control Conference, Shanghai, P.R. China, pp. 3980-3986, Dec. 16-18, 2009.
Zelenka, et al., "An Active Regeneration as a Key Element for Safe Particulate Trap Use," SAE Paper No. 2001-0103199, 13 pages, Feb. 2001.
Zhu, "Constrained Nonlinear Model Predictive Control for Vehicle Regulation," Dissertation, Graduate School of the Ohio State University, 125 pages, 2008.

* cited by examiner

Fig. 1A

| Parameter Name | Parameter Units |
|---|---|
| Catalyst length | [m] |
| Catalyst diameter | [m] |
| Housing wall thickness | [m] |
| Frontal flow area | [m2] |
| Molar weight of gas | [kg/mol] |

Fig. 1B

| Parameter Name | Parameter Units |
|---|---|
| Gas/monolith surface | [m2] |
| Hydraulic diameter | [m] |
| Specific heat of monolith | [J/K/kg] |
| Monolith mass | [kg] |
| Thermal conductivity to ambient | [W/K/m] |

Fig. 1C

| Parameter Name | Parameter Units |
|---|---|
| Adsorption rate coefficient | [-] |
| Desorption pre-exponential factor | [-] |
| Desorption activation energy | [J/mol] |
| Catalyst capacity (sites) | [mol] |

Fig. 1D

| Parameter Name | Parameter Units |
|---|---|
| Pre-exponential factor | [-] |
| Activation energy | [J/mol] |
| Reaction rate exponents | [-] |
| Heat of reaction | [J/mol] |

Fig. 4

| Parameter Name | Units | Default value | Range | Type |
|---|---|---|---|---|
| Catalyst length | [m] | | | Constant |
| Catalyst diameter | [m] | | | Constant |
| Housing wall thickness | [m] | | | Constant |
| Molar weight of gas | [kg/mol] | | | Constant |
| Channel cross section area | [m2] | | | Constant |
| Channel density | [cells/m2] or [cpsi] | | | Constant |
| Frontal flow area* | [m2] | | | ID |
| Catalyst effective volume* | [m3] | | | ID |
| Number of cells* | [-] | | | Constant |

Fig. 5

| Parameter Name | Units | Default value | Range | Type |
|---|---|---|---|---|
| Monolith mass | [kg] | | | Constant |
| Heat transfer correction factor from monolith to ambient*** | [-] | | | Constant |
| Heat transfer correction factor from gas to monolith** | [-] | | | Editable, ID |
| Specific heat of monolith* | [J/K/kg] | | | Editable, ID |
| Thermal conductivity to ambient | [W/K/m] | | | Constant in mask only |
| Hydraulic diameter | [m] | | | Constant in mask only |
| Characteristic dimension of convection | [m] | | | Constant in mask only |

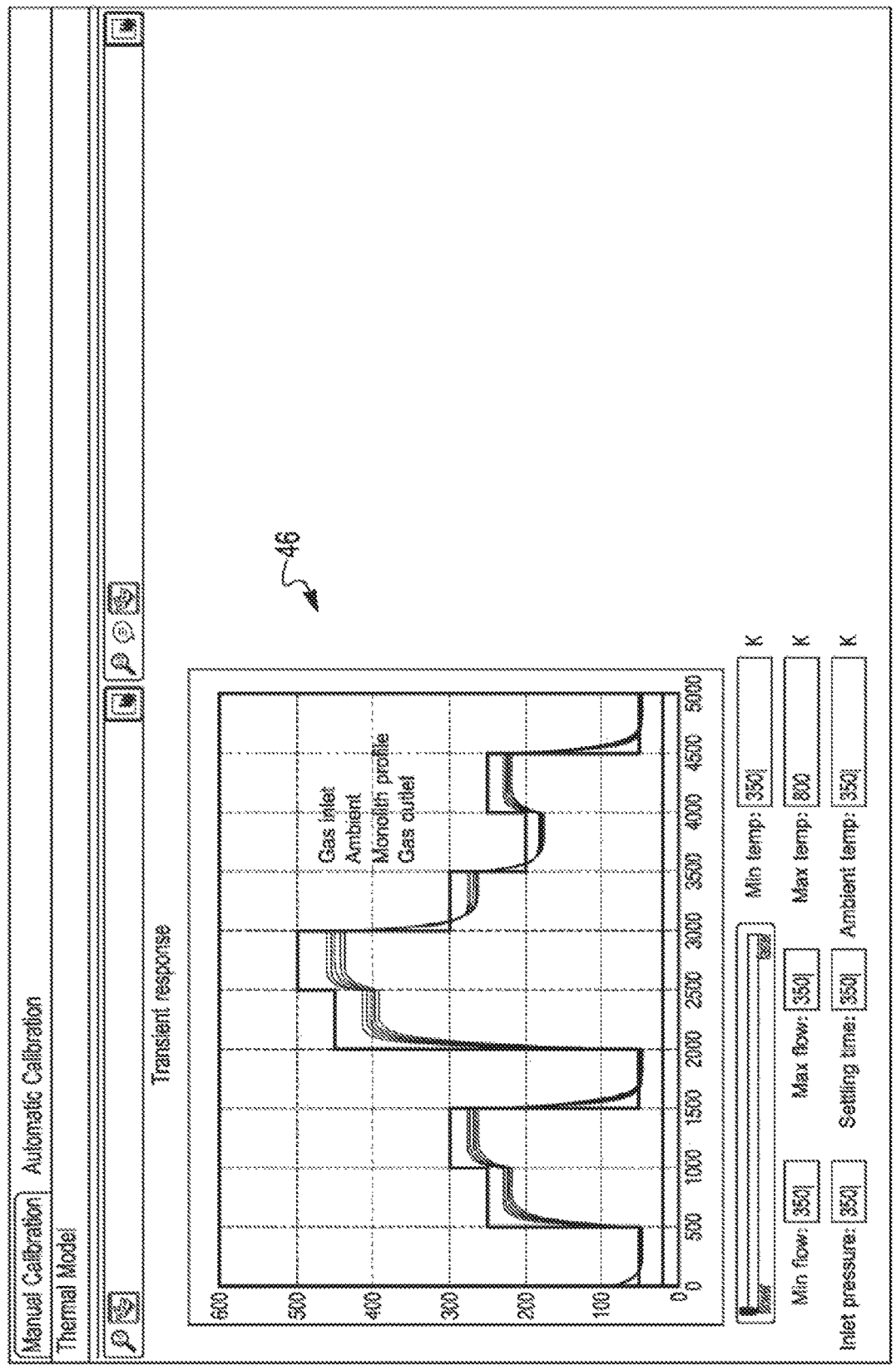

Fig. 9

| Parameter Name | Units | Default value | Range | Type |
|---|---|---|---|---|
| Adsorption rate exponents** | [-] | | | Constant |
| Adsorption pre-exponential factor | [-] | | | Editable, ID |
| Desorption pre-exponential factor | [-] | | | Editable, ID |
| Desorption activation energy | [J/mol] | | | Editable, ID |
| Catalyst capacity (sites)* | [mol] | | | Editable, ID |

Fig. 13

| Parameter Name | Units | Default value | Range | Type |
|---|---|---|---|---|
| Pre-exponential factor | [-] | | | Editable, ID |
| Activation energy | [J/mol] | | | Editable, ID |
| Reaction rate exponents | [-] | | | Editable, ID |
| Heat of reaction | [J/mol] | | | Editable, ID |
| Diffusion parameters for temperature* | [-] | | | ID |
| Diffusion parameters for velocity* | [-] | | | ID |

Fig. 17

| Parameter Name | Units | Default value | Range | Type |
|---|---|---|---|---|
| Pre-exponential factor | [-] | | | Editable, ID |
| Activation energies | [J/mol] | | | Editable, ID |
| Reaction rate exponents | [-] | | | Editable, ID |
| Heat of reactions | [J/mol] | | | Editable, ID |
| Diffusion parameters for velocity | [-] | | | ID |
| Diffusion parameters for temperature | [-] | | | ID |
| Inhibition parameters of Custom function 1* | [-] | | | ID |
| Inhibition parameters of Custom function 2* | [-] | | | ID |

Fig. 29

| Parameter Name | Units | Default value | Range | Scale |
|---|---|---|---|---|
| Frontal flow area | [m2] | | | linear |
| Catalyst effective volume | [m3] | | | linear |
| Heat transfer correction factor from gas to monolith | [-] | | | linear |
| Specific heat of monolith** | [j/K/kg] | | | log |
| Adsorption pre-exponential factors | [-] | | | log |
| Adsorption rate exponents* | [-] | | | linear |
| Desorption pre-exponential factors | [-] | | | log |
| Desorption activation energies | [J/mol] | | | log |
| Catalyst capacity (sites)** | [mol] | | | linear |
| Pre-exponential factors | [-] | | | log |
| Activation energies | [J/mol] | | | log |
| Reaction rate exponents | [-] | | | linear |
| Heat of reactions | [J/mol] | | | log |
| Diffusion parameters for velocity | [-] | | | linear |
| Diffusion parameters for temperature | [-] | | | linear |
| Inhibition parameters of Custom function 1 | [-] | | | log |
| Inhibition parameters of Custom function 2 | [-] | | | log |

US 11,687,688 B2

APPROACH FOR AFTERTREATMENT SYSTEM MODELING AND MODEL IDENTIFICATION

This application is a divisional of U.S. patent application Ser. No. 15/019,029, filed Feb. 9, 2016, which claims priority to European Patent Application 15155295.7, filed Feb. 16, 2015. U.S. patent application Ser. No. 15/019,029, filed Feb. 9, 2016, is hereby incorporated by reference.

BACKGROUND

The present disclosure pertains to engines with aftertreatment mechanisms, and particularly to models of them

SUMMARY

The disclosure reveals a system and approach for catalyst model parameter identification with modeling accomplished by an identification procedure that may incorporate a catalyst parameter identification procedure which may include determination of parameters for a catalyst device, specification of values for parameters and component level identification. Component level identification may be of a thermal model, adsorption and desorption, and chemistry. There may then be system level identification to get a final estimate of catalyst parameters.

BRIEF DESCRIPTION OF THE DRAWING

FIG. 1a is a diagram of a table listing of basic catalyst parameters and constants;

FIG. 1b is a diagram of a table that lists parameters pertinent to a thermal model;

FIG. 1c is a diagram of a table that lists parameters relevant for adsorption and desorption;

FIG. 1d is a diagram of a table of parameters pertaining to chemical reactions;

FIG. 4 is a diagram of a table listing parameters for a catalyst component;

FIG. 5 is a diagram of a table listing parameters for a thermal model;

FIG. 6 is a diagram of a plot of a thermal model having a transient response with manual calibration;

FIG. 9 is a diagram of a table listing of adsorption and desorption with parameters for a particular adsorbent, relative to component level identification;

FIG. 13 is a diagram of a table showing parameters relative to separable reactions for component level identification;

FIG. 17 is a diagram of a table parameters for not separable reactions of component level identification;

FIG. 29 is a diagram of a table showing parameters for a system level identification;

DESCRIPTION

Figure 1:
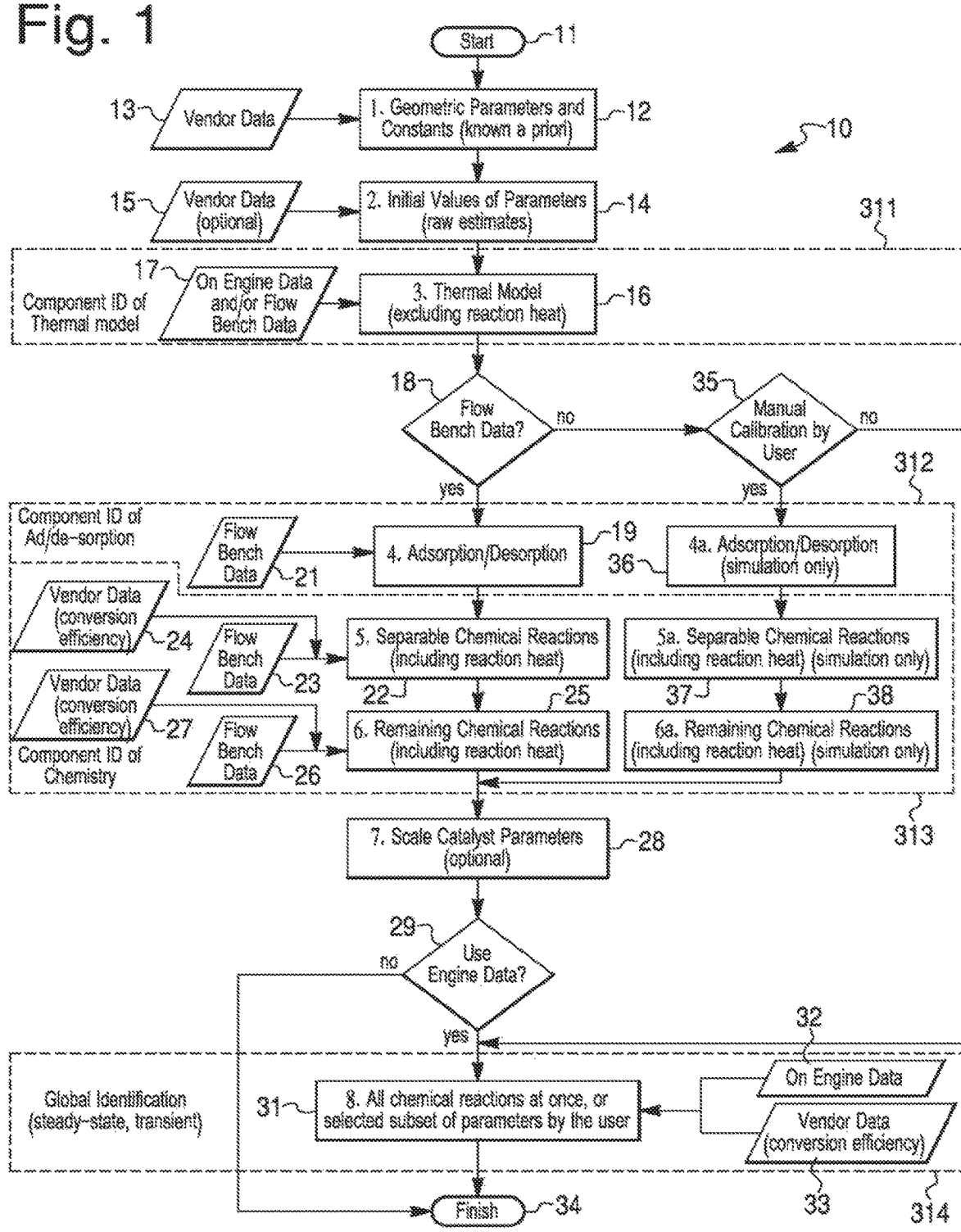
FIG. 1 is a diagram of a basic workflow chart.

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

Internal combustion engines appear as a significant source of exhaust pollutants and there appears a trend to reduce the emissions as much as possible. The limits may be prescribed by various emission standards, e.g., in Europe known as EURO. To achieve the emission limits, there appears a need to introduce new technologies and innovations. Typical monitored pollutants may include nitric oxide (NO), nitric dioxide (NO2), hydrocarbons (HC), carbon monoxide (CO), particulate matter (PM), and so forth. Various technologies may be used to reduce these pollutants, for example, exhaust gas recirculation (EGR) may have been introduced to significantly reduce NOx for diesel engines. In general, there may be some approaches in how to influence the pollutants that 1) incorporate preventing a forming of the pollutants beyond a set amount, and 2) reduce the already produced pollutants.

The first approach may mean that the engine produces less than or equal to an allowed amount of monitored emissions. This appears possible to a certain threshold only and it is not free as a cost is decreased fuel economy. Limitations for further reduction by this approach may incorporate technological and physical limits of the combustion process and overall engine efficiency. On the other hand, this approach may require slight modification of the engine only (exhaust gas recirculation) without extra hardware.

The second approach may require additional equipment to reduce the engine out pollutants. An idea may be to let an engine produce certain amount of pollutants, but the pollutants might be immediately reduced by an aftertreatment line. The advantage may be an improvement of fuel economy of the engine itself. On the other hand, aftertreatment systems may be required, which means additional costs for the engine applications. Furthermore, some aftertreatment systems (e.g., selective catalytic reduction (SCR), diesel oxidation catalyst (DOC) or selective catalytic reduction on-filter (SCRF)) may need to use a reduction agent (e.g., ammonia or urea), and this can imply an additional cost that should be considered when computing an overall engine fuel (or fluid) economy.

An introduction of SCR to reduce NOx may be a challenge from a control point of view and can be a candidate for an advanced control system approach. An engine together with an aftertreatment system may be a system which needs precise control. Engine overall optimization may be achieved by using an advanced control system approach and various optimization approaches, e.g., model based predictive control (MPC). The advanced control system may be model based and thus may appear necessary to deal with engine and aftertreatment system modeling.

Mathematical modeling of a catalyst (e.g., SCR, SCRF, LNT or DOC) for automotive applications may also cover a parameter identification procedure. An existence of an automatic parameter identification procedure of a catalyst model may be important for a practical mathematical model. The procedure should be as simple as possible, be robust and need to provide results with required accuracy for a given application. Practical identification procedures may be obtained by formulating the identification procedure as a mathematical optimization problem. The present approach may provide for a catalyst parameter identification.

A catalyst for automotive applications may be a device with highly nonlinear behavior. A modeling and model identification approach may be used. The model may have a number of parameters. An approach to identify these parameters may use some nonlinear optimization approach, and to identify virtually all the parameters at once. Such approach is not necessarily suitable for several reasons. Namely, there may be a possibility of existence of local extreme points. Nonlinearity may cause numerical instabilities or the optimization problem could be too large and therefore it may take much time to get some reasonable solution.

In addition, if measured data for the model fitting is taken just from on-engine experiments, certain key behaviors of the device may be difficult to observe due to the interdependencies of the input properties to the catalyst.

The following present approach may be used. The identification procedure may be broken into several smaller and better defined identification sub-issues. The present approach for a catalyst parameter identification may have main phases. Phase 1 may be a specification of initial values of parameters. Phase 2 may be a so-called component level identification. Phase 3 may be seen as a system level identification. Furthermore, the latter two phases may be divided into a steady state identification and a transient identification.

Component level identification of phase 2 may be performed by collecting data from a chemical flow bench or by other suitable approach. The flow bench may enable one to prepare an exhaust gas composition as needed by the experiment, and thus appear suitable for the component level identification. System level identification of phase 3 may be achieved by using exhaust gas engine out data.

Phase 1 may involve initial values of parameters (without data). Phase 1 may be where a user is asked to prepare the initial values of virtually all parameters for the catalyst. This phase may be a significant part as it could influence performance of the automatic tuning procedure. The automatic tuning procedure may be a numerical solution of an optimization task. It may start from some initial conditions and then iterate to a local optimal solution which is close to the starting point. If the starting point is close to the global optimal solution, then the optimization procedure may find the global optimal solution. The initial values specified by a user during this phase may be a starting point for Phase 2.

Phase 2 may be component level identification (using, e.g., data from a flow bench). The catalyst model may have a few basic components which can be seen as individual components since their parameters may be identified independently on the other components. The basic individual components may incorporate a 1) thermal subsystem or thermal model, 2) adsorption and desorption, and 3) chemical reactions.

The thermal subsystem may cover namely heat transfer in the catalyst. Assume an SCR system. In the SCR, the influence of chemical reactions to the thermal behavior may be negligible and therefore the parameters of this subsystem can be identified separately on other subsystems. The parameters may be, namely, heat transfer coefficients between gas, monolith, housing and ambient, and other parameters that influence the thermal behavior.

Adsorption and desorption may be of, for example, ammonia (a reductant) in the catalyst washcoat for various temperatures. To collect needed data, flow bench equipment may have to be used.

A few chemical reactions with a few parameters may need to be estimated. The parameters may be, namely, related to the reaction rates, e.g., pre-exponential factors, activation energy, reaction order, reaction rate exponents, heat of reaction, and so forth. Reactions considered in the SCR catalyst may be referred to as a standard SCR reaction, fast SCR reaction, slow SCR reaction, urea decomposition and ammonia oxidation. If there is just one pollutant in a reaction, e.g., a standard SCR reaction NO, then the reaction may be seen as one component and its parameters can be identified independently on other components, e.g., by using the flow bench data. Phase 2 results may be used as a starting point for phase 3. Phase 3 may be for system level identification.

To reiterate, the present approach may be implemented as a series of steps with some executed in an engine laboratory and others executed by a computer program The steps may be used as in the following: 1) Prepare and configure the catalyst mathematical model with virtually all needed components for an engine application; 2) (Phase 1) Estimate the initial values of virtually all needed parameters based on literature and the user's experiences; 3) Select the individual catalyst model components (thermal subsystems, adsorption and desorption subsystem, chemical reactions, and so forth), and design the identification experiments for the flow bench to get virtually all needed data for component level identification; 4) Set up the flow bench with the real catalyst for the experiments, perform the experiments and collect the needed data; 5) (Phase 2) Perform the component level identification based on the flow bench data; 6) Design the identification experiment for the catalyst model system level identification where the experiment may be based on the real catalyst connected with the engine; 7) Set up the engine with the catalyst device on the test bench and perform the experiments to collect required data; 8) (Phase 3) Perform the system level identification of the catalyst model to get a final set of catalyst model parameters.

An objective may be to sketch a high overview of an identification procedure for aftertreatment systems, namely, DOC, SCR and SCRF catalysts. A catalyst model structure may be noted. A catalyst model may have several parts that can be handled as individual components. One component may incorporate a thermal model that includes, namely, heat transfer from gas to monolith, from monolith to housing and from housing to ambient. Another component may incorporate adsorption and desorption that includes storage of chemical species for reaction, for instance, ammonia for SCR and oxygen for DOC. This component may be also used to model hydrocarbon storage for a DOC cold start. An additional component may incorporate a chemistry that includes chemical reactions and a reaction mechanism.

An identification concept may be noted. Identification should be simple, user friendly and an amount of needed data should be minimized. Several possible sets of data may incorporate information provided by a catalyst producer, flow bench data and on-engine data. A basic workflow chart 10 is shown in FIG. 1.

Geometric parameters and constants may be noted. Fixed physical parameters may be such parameters that are known or can be directly measured. The basic needed parameters may be catalyst length, catalyst diameter, housing wall thickness, frontal flow area and molar weight of gas, as listed in a table of FIG. 1a.

Initial values of parameters may be noted. This step in workflow chart 10 may represent a specification of initial values for virtually all parameters. One may see that there should be defined some default values for a case where a user is unable to specify any value.

The thermal model may be noted. The thermal model may include namely heat transfer from exhaust gas to monolith and from monolith to ambient through catalyst housing. This may be a first step where the parameters are estimated from data automatically. The data may be on-engine or flow bench. One may note that reactions with significant reaction heat need to be suppressed relative to virtually all data for this step. The pertinent parameters may be gas/monolith surface, hydraulic diameter, specific heat of monolith, monolith mass and thermal conductivity to ambient, as listed in a table of FIG. 1b.

Adsorption and desorption may be noted. Adsorption and desorption may be estimated independently just when the flow bench data are available, otherwise they may need to be estimated together with (virtually all) chemical reactions. The parameters such as adsorption rate coefficient, desorption pre-exponential factor, desorption activation energy and catalyst capacity (sites), as shown in a table of FIG. 1c, may be relevant for adsorption and desorption.

Separable chemical reactions may be noted. Separable chemical reactions may be such reactions that can be isolated from the others during the identification experiment (only one reaction takes place). An example of separable chemical reaction in SCR catalyst may be:

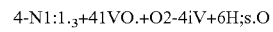

Parameters for each chemical reaction, such as pre-exponential factor, activation energy, reaction rate exponents and heat of reaction, may be listed in a table of FIG. 1d.

Remaining chemical reactions may be noted. This step may include identification of chemical reactions that cannot be separated, or corresponding flow bench data that are unavailable. The parameters for each remaining chemical reaction may be the same as for separable chemical reactions, as listed in the table of FIG. 1d.

Scaling catalyst parameters may be noted. This may be an optional step that is used to scale the catalyst. It may be a usual practice that just one block of catalyst is used on the flow bench and then that the model is scaled by using appropriate catalyst parameters (e.g., catalyst length, diameter, volume, housing wall thickness, frontal flow area, molar weight of gas, and so on).

All or selected parameters may be noted. This step may be used whenever the flow bench data are unavailable, or to improve a fit by using the particular engine data. It may be assumed that any subset of parameters for identification can be selected by a user. This part may be the most flexible one in a sense of degrees of freedom Identification by using steady state data may be noted. Steady state identification may be used in any step in the identification procedure. It may be fast and provide a good initial estimate for a transient identification part.

Identification by using transient data may be noted. Transient identification may be used in any step of the identification procedure. Transient identification should follow the steady state identification as the steady state identification may provide a good initial estimate for a transient identification.

A catalyst identification workflow may be noted in a chart 10 of FIG. 1. From start 11, geometric parameters and constants at block 12 may obtained from vendor data 13. The parameters and constants may be a priori knowledge. Initial values of parameters may be obtained at block 14 from optional vendor data 15. The values may be raw estimates.

Component level identification (ID) of a thermal model 311 may be determined. A thermal model (excluding reaction heat) may be obtained at block 16 from on engine data and/or flow bench data 17.

As component level identification of adsorption/desorption 312 approaches, a question at symbol 18 may be asked as to whether flow bench data is to be used. If an answer is yes, then adsorption/desorption reactions may be noted at block 19 from flow bench data 21. As component level identification of chemistry 313 approaches, separable chemical reactions (including reaction heat) may be noted at block 22 from flow bench data 23 along with vendor data 24 with conversion efficiency. Remaining chemical reactions (including reaction heat may be noted at block 25 from flow bench data 26 along with vendor data 27 with conversion efficiency. Optionally, at block 28, catalyst parameters may be scaled.

At symbol 29, a question may be asked concerning whether engine data is to be used. If an answer is yes, then system level identification 314 of a steady state or transient nature can be proceeded to with all chemical reactions at once, or a selected subset of parameters may be used as noted at block 31. On engine data 32, and vendor data 32 with conversion efficiency 33 may be provided to block 31. Then the workflow may be finished at symbol 34.

If the answer to the question at symbol 29 is no, then the workflow may be finished at symbol 34.

If the answer to the question at symbol 18 is no relative to use of flow bench data, then a question whether a user is to use manual calibration at symbol 35. If the answer to the question is no, then proceeding to block 31 may be done. If the answer to the question is yes, then adsorption/desorption component level identification may be attained at block 36 with simulation only. Component level identification of chemistry may achieved with separable chemical reactions including reaction heat by simulation only at block 37 and the remaining chemical reactions including reaction heat at block 38 by simulation only at block 38. Then the catalyst parameters may be optionally scaled at block 28. The procedure may continue at symbol 29 and beyond as indicated herein.

The order of steps for a component level identification is needed for the catalyst identification workflow.

Data set types for the component level identification may incorporate global steady state/transient data and flow bench data. The global steady state data may incorporate that of all reactions and on-engine experiments. The flow bench data may incorporate only some set of reactions in progress for each individual separable reaction and for each adsorption/desorption reaction. Conversion efficiency may be noted for a particular reaction.

Figure 2:
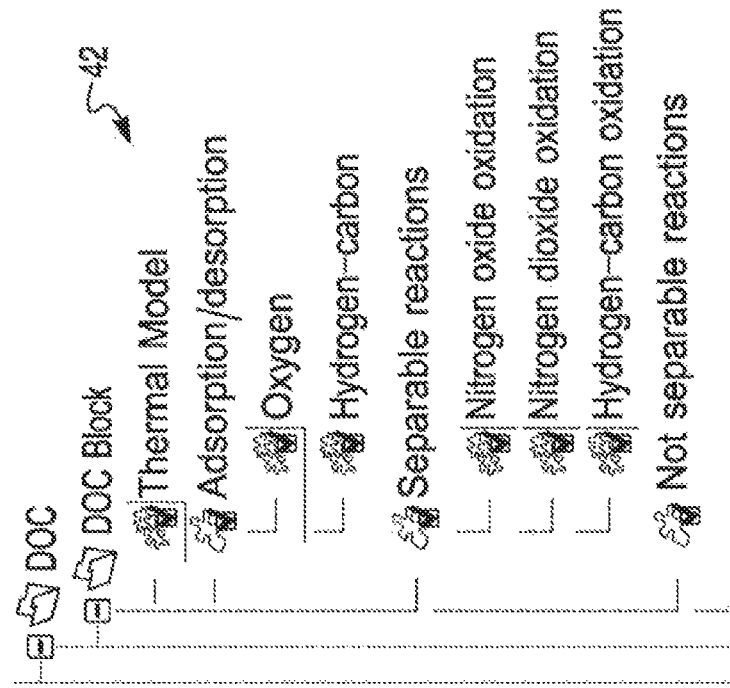
FIG. 2 is a diagram of a component catalyst tree for a selective catalytic reduction (SCR) catalyst

A component catalyst tree 41 for an SCR catalyst may be shown in FIG. 2. Tree 41 may indicate the thermal model, adsorption/desorption reactions of ammonia, separable reactions of ammonia oxidation, SCR NO2 reaction and a standard SCR reaction. Not separable reactions may incorporate a fast SCR reaction.

Figure 3:
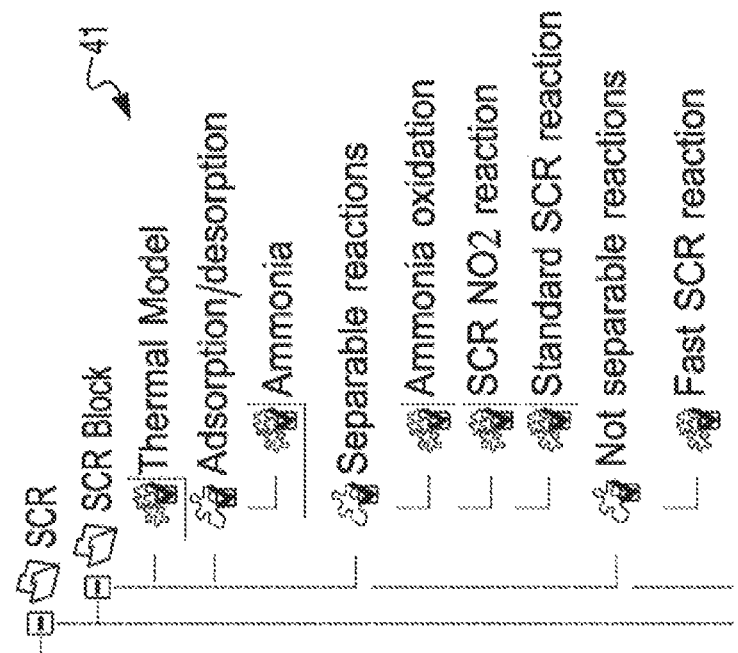
FIG. 3 is a diagram of a component catalyst tree for a diesel oxidation catalyst (DOC)

A component catalyst tree 42 for DOC may be shown in FIG. 3. Tree 42 may indicate the thermal model, adsorption/desorption reactions of oxygen and hydrogen-carbon, and separable reaction of NO oxidation, CO oxidation and HC oxidation. There are not necessarily any separable reactions.

FIG. 4 shows a table 44 of parameters for a catalyst component. Just general catalyst parameters are incorporated, such as catalyst length, diameter, housing wall thickness, molar weight of gas, channel cross section area, channel density, frontal area, catalyst effective volume and a number of cells. One star in the table means that frontal flow area and catalyst effective volume may be computed from the other parameters, or if they are not defined, a raw estimate may be set. Two stars mean that the number of cells may be set to a default value and set to be hidden.

FIG. 5 shows a table 45 of parameters for a thermal model. The parameters may incorporate monolith mass, heat transfer correction factor from monolith to ambient. Specific heat of the monolith is a parameter that influences only dynamic behavior. The parameters may also include thermal conductivity to ambient, hydraulic diameter and characteristic dimension of convection.

The component level identification of the thermal model may have data sets with no reaction heat, and can be steady state or transient. Signals that may be needed are, e.g., inlet/outlet temperature, inlet pressure, inlet flow and ambient temperature.

A steady state identification may incorporate a scatter plot and Coefficient of Determination (CoD). A transient identification may incorporate a plot with signal comparison such as catalyst dynamics.

FIG. 6 is a diagram of a plot 46 of a thermal model with manual calibration. A simulation may involve a random or predefined inlet temperature profile. Plot 46 shows gas inlet, ambient, monolith profile and gas outlet.

Figure 7:
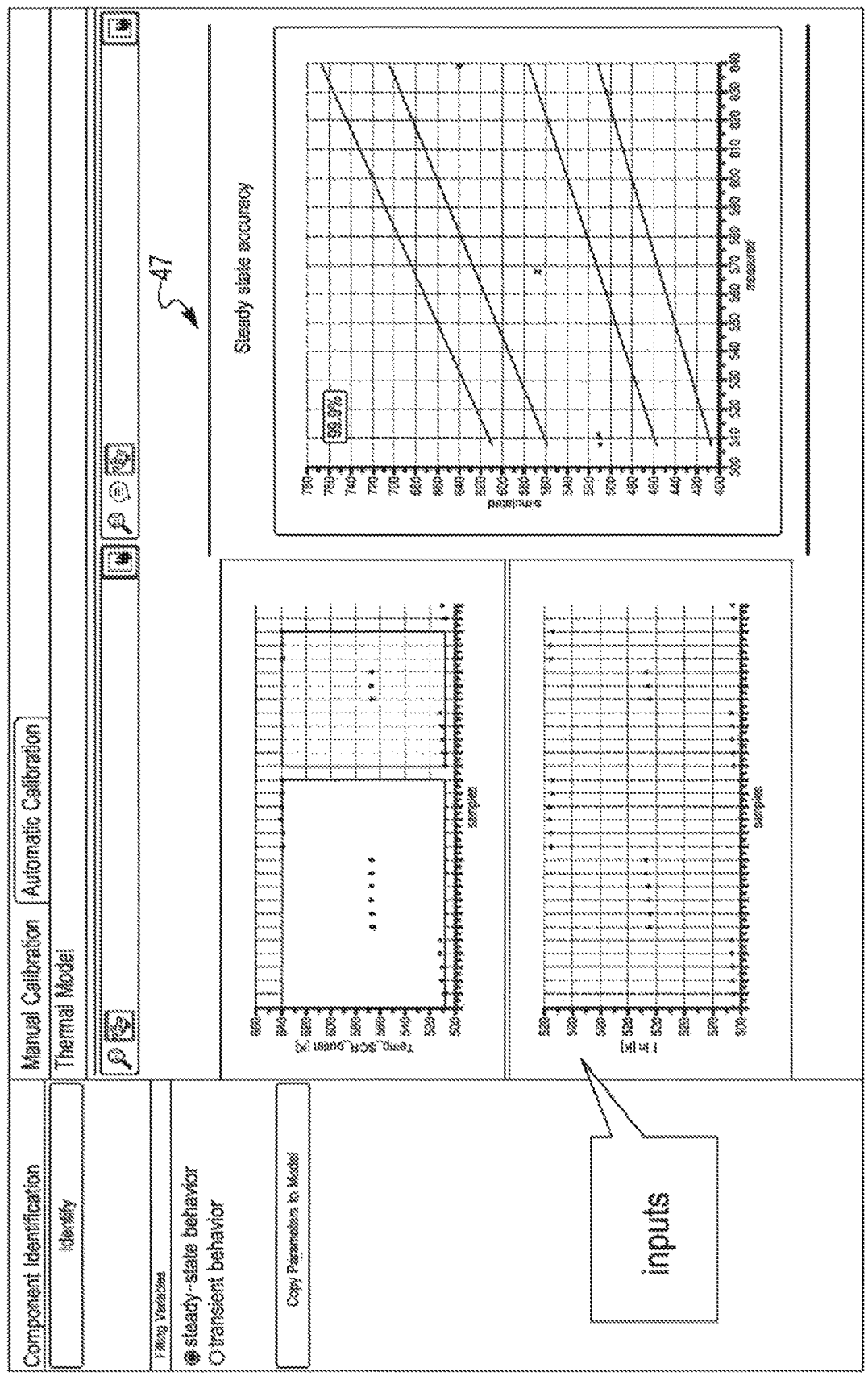
FIG. 7 is a diagram of a plot of a thermal model having a steady state response with automatic calibration.
Figure 8:
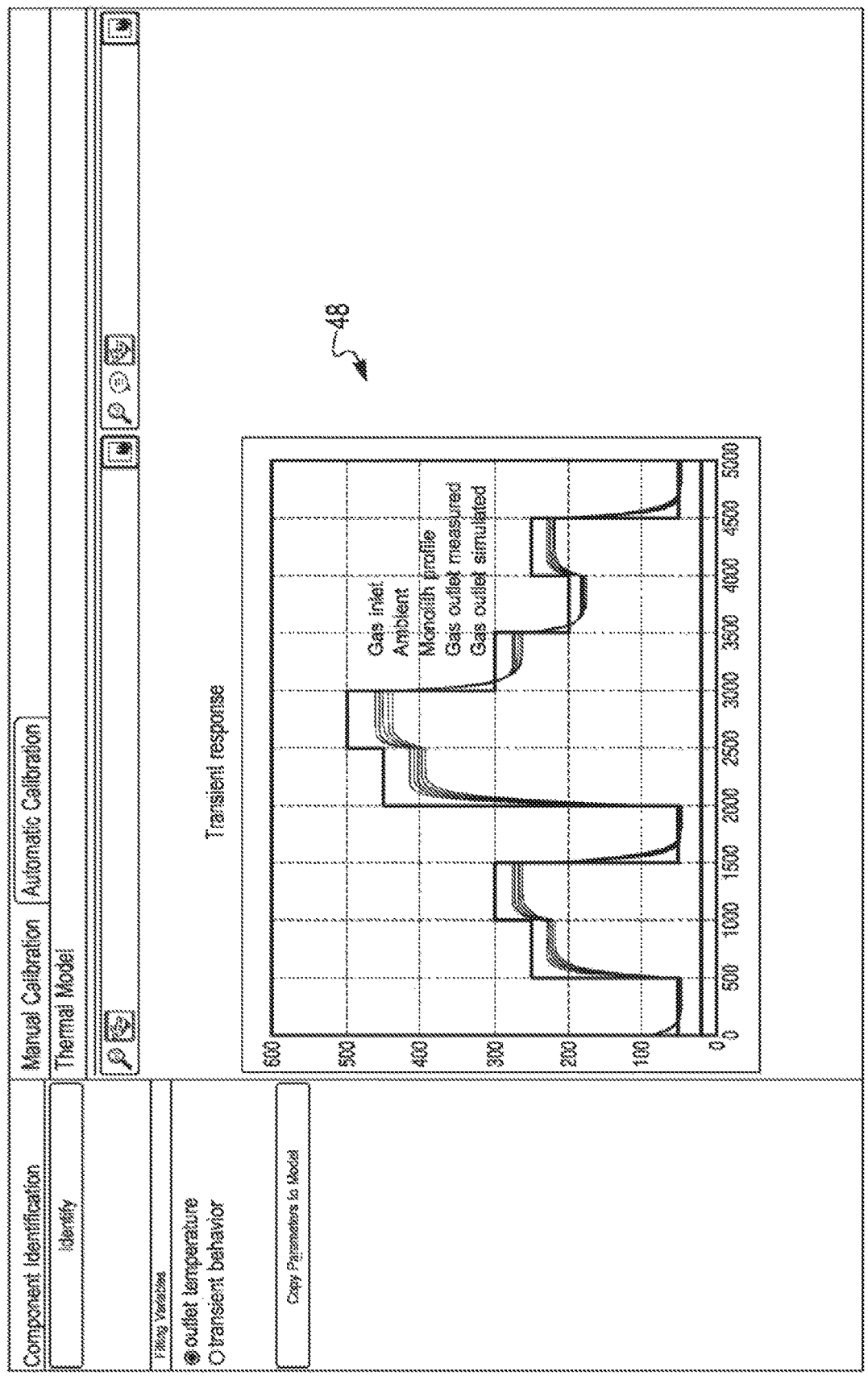
FIG. 8 is a diagram of a plot of a thermal model having a transient response with automatic calibration.

FIG. 7 is a diagram of a plot of the thermal model with automatic calibration. The identification may proceed automatically with a steady state and after that with a transient identification in a plot 48 in a diagram of FIG. 8. The parameters may incorporate gas inlet, ambient, monolith profile, gas outlet measured, and gas outlet simulated.

FIG. 9 shows a table 49 of adsorption/desorption with parameters for a particular adsorbent, relative to component level identification. The parameters may incorporate adsorption rate exponents. The adsorption rate exponents may be assumed virtually always as a fixed value. The parameters may also incorporate an adsorption pre-exponential factor, a desorption pre-exponential factor, a desorption activation energy, and a catalyst capacity (sites) that may be a parameter that influences only dynamic behavior.

The component level identification may involve an adsorption/desorption model having flow bench data sets. An only absorbent present in a flow may be some inert gas such as N2. The data sets may be that of flow bench steady state, flow bench transient, and a storage curve. Signals that may be needed involve inlet temperature, inlet pressure, inlet flow, inlet/outlet concentration of absorbent, and ambient temperature. The identification process may be a steady state identification and a transient identification. The transient identification may incorporate sensor dynamics and catalyst dynamics.

Figure 10:
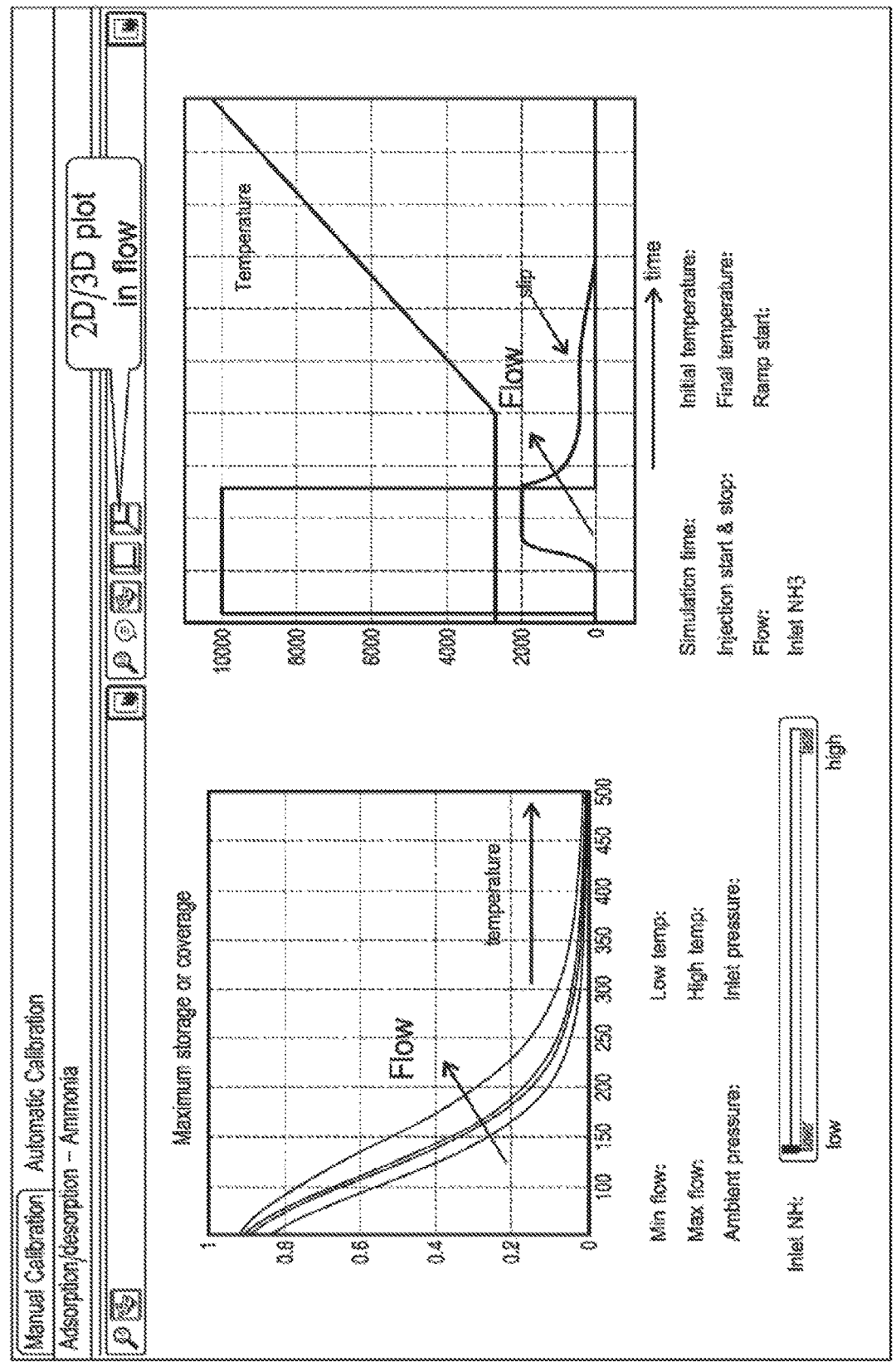
FIG. 10 shows diagrams of graphs revealing adsorption and desorption activity with manual calibration for component level identification.

FIG. 10 is a diagram of graph 51 revealing adsorption/desorption activity with manual calibration for component level identification.

Figure 11:
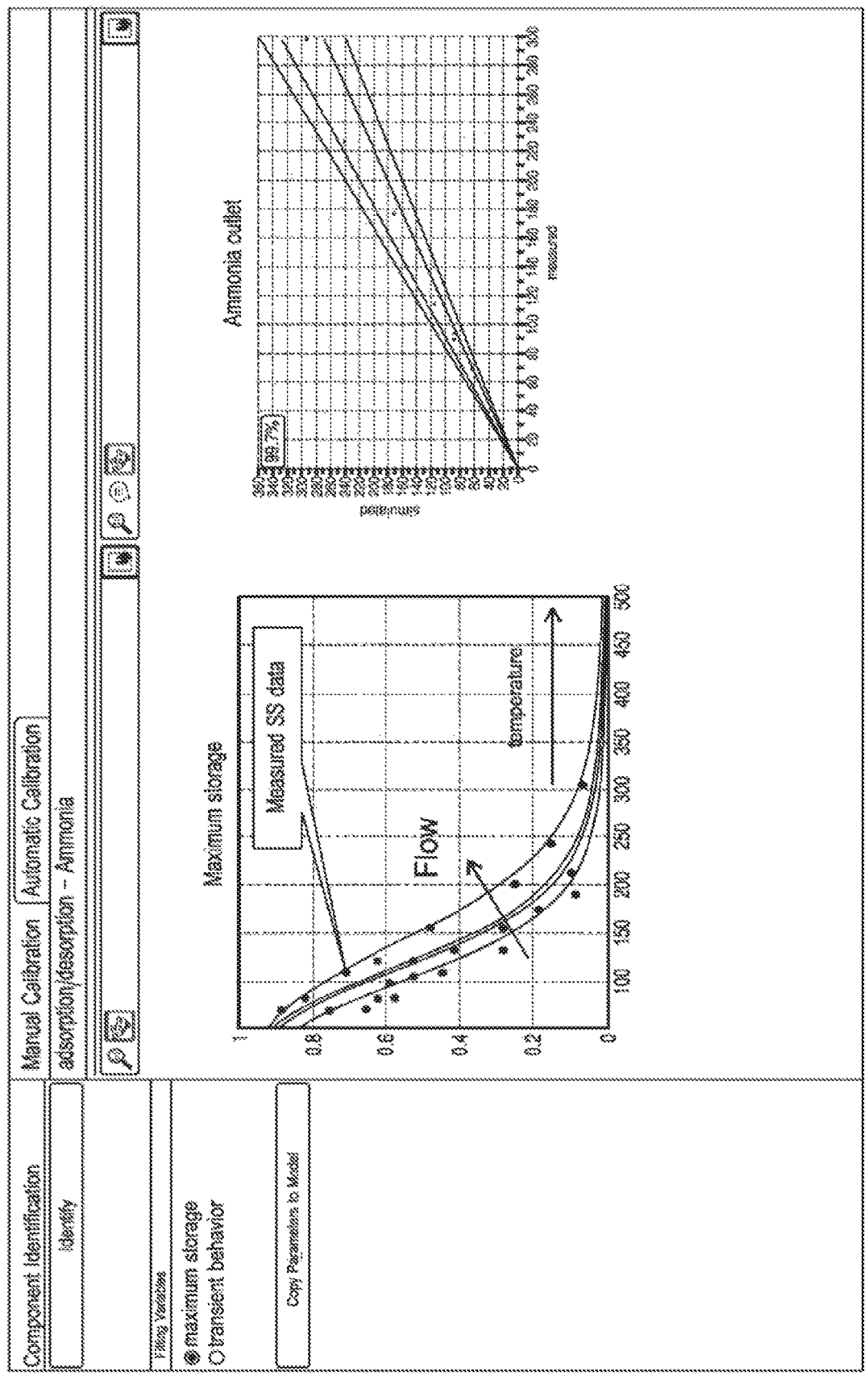
FIG. 11 is a diagram of graphs for component level identification of adsorption and desorption with automatic calibration of storage capacity based on measured ammonia outlet.
Figure 12:
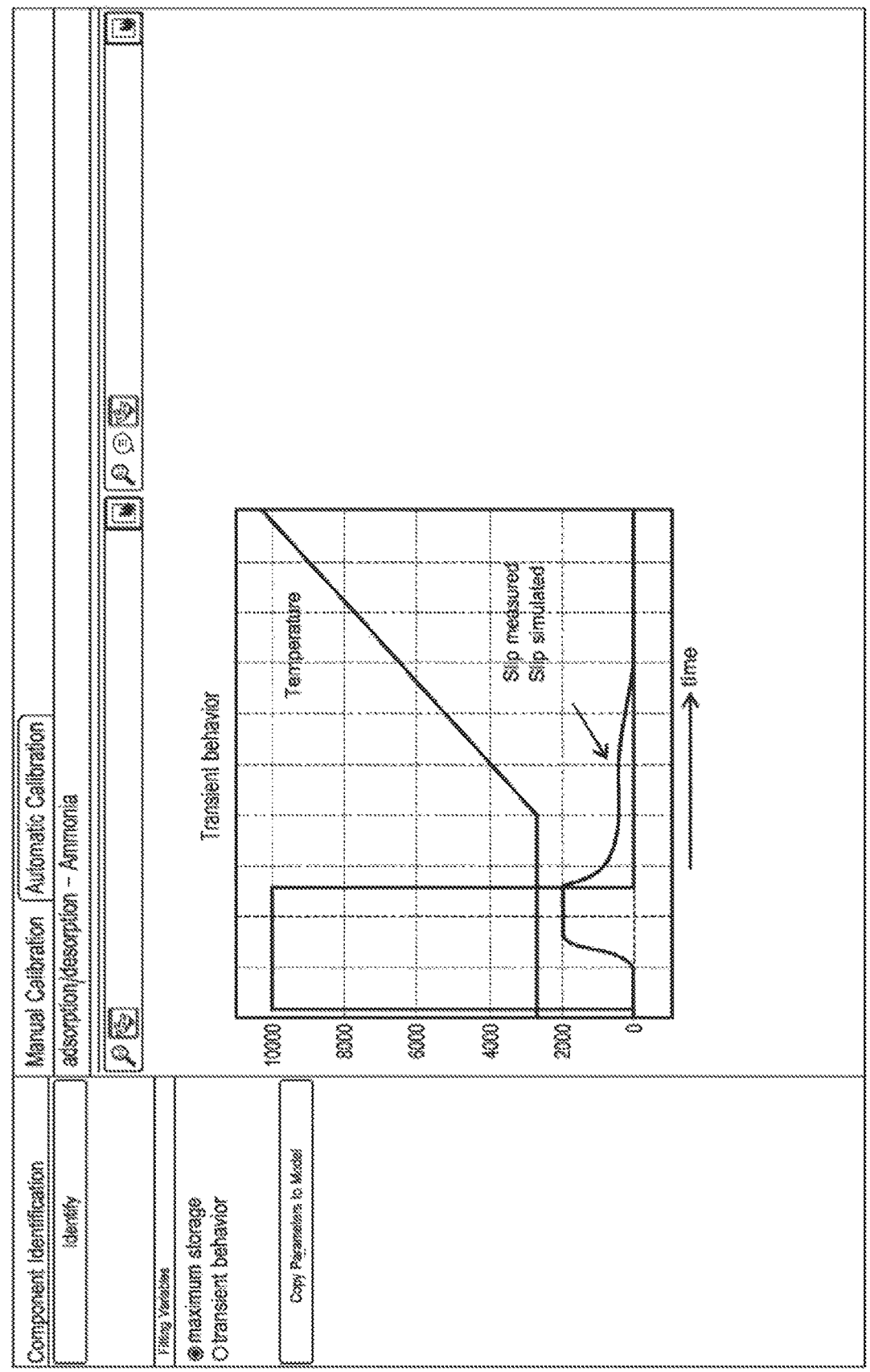
FIG. 12 is a diagram of a graph for component level identification of adsorption and desorption with automatic calibration relative to transient behavior.

FIG. 11 is a diagram of graphs 52 for component level identification of adsorption/desorption with automatic calibration relative to maximum storage and ammonia outlet. FIG. 12 is a diagram of graph 53 for component level identification of adsorption/desorption with automatic calibration relative to transient behavior. In graphs 52 and 53, identification may proceed automatically with steady state and after that with transient identification. FIG. 13 is a diagram of a table 54 showing parameters relative to separable reactions for component level identification. The parameters may incorporate a pre-exponential factor, activation energy, reaction rate exponents, and heat of reaction. Also, the parameters may incorporate diffusion parameters for temperature and diffusion for velocity that are parameters related to species and not the reaction itself.

Separable reactions for component level identification may have data sets relating to steady-state (flow bench) and an efficiency curve for a particular reaction. Signals needed may incorporate inlet/outlet temperature, inlet pressure, inlet flow, inlet concentration of adsorbent, inlet/outlet concentration of species participating in reaction, and ambient temperature. An identification process may be of a steady state.

Figure 14:
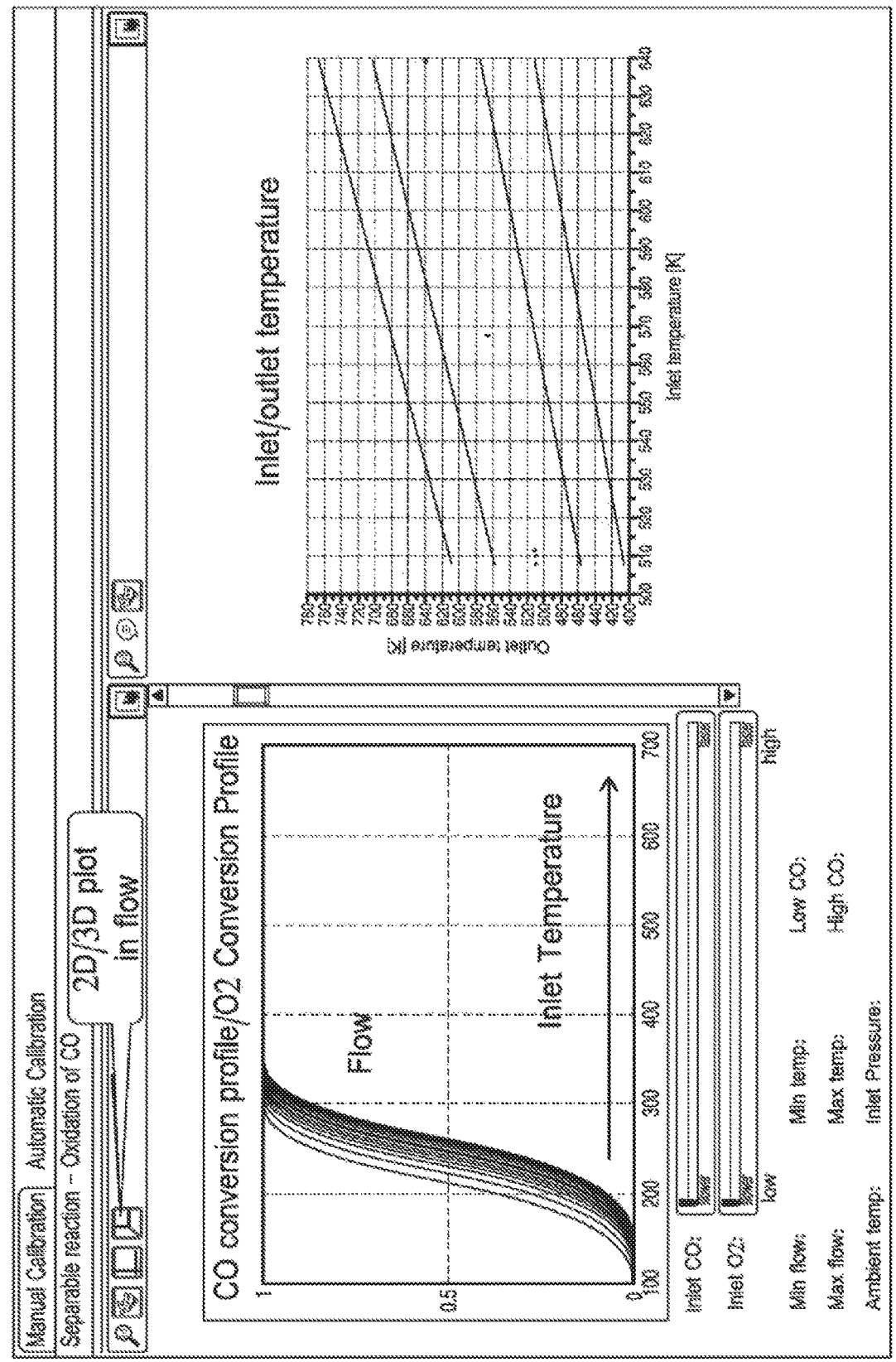
FIG. 14 is a diagram of graphs of plots for separable reactions with manual calibration for component level identification.

FIG. 14 is a diagram of graphs 55 of plots for separable reactions with manual calibration for a conversion profile of CO and O2, for component level identification.

Figure 15:
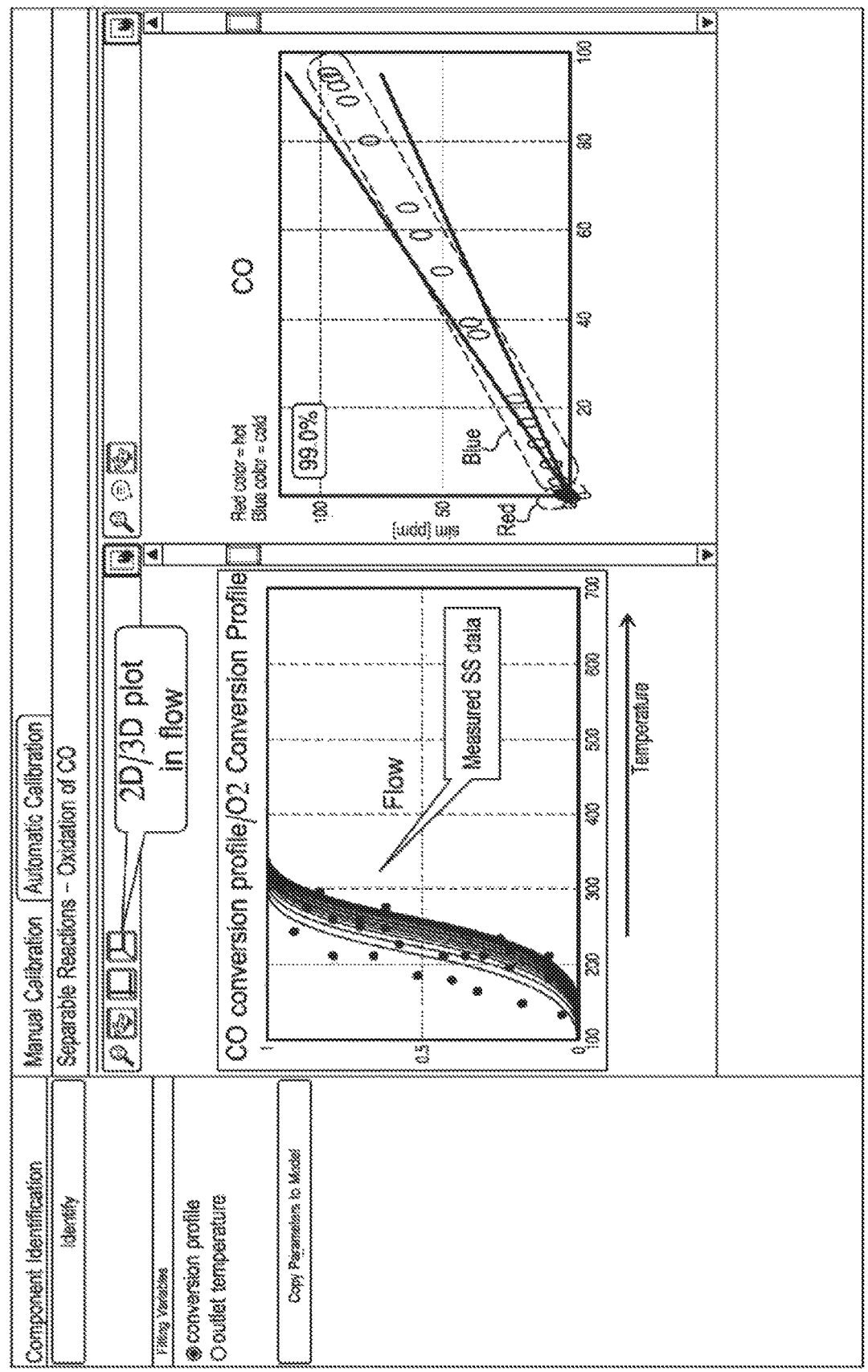
FIG. 15 is a diagram of graphs of plots for separable reactions with automatic calibration for component level identification.

FIG. 15 is a diagram of graphs 57 of plots for separable reactions with automatic calibration for a conversion profile of CO and O2, for component level identification.

Figure 16:
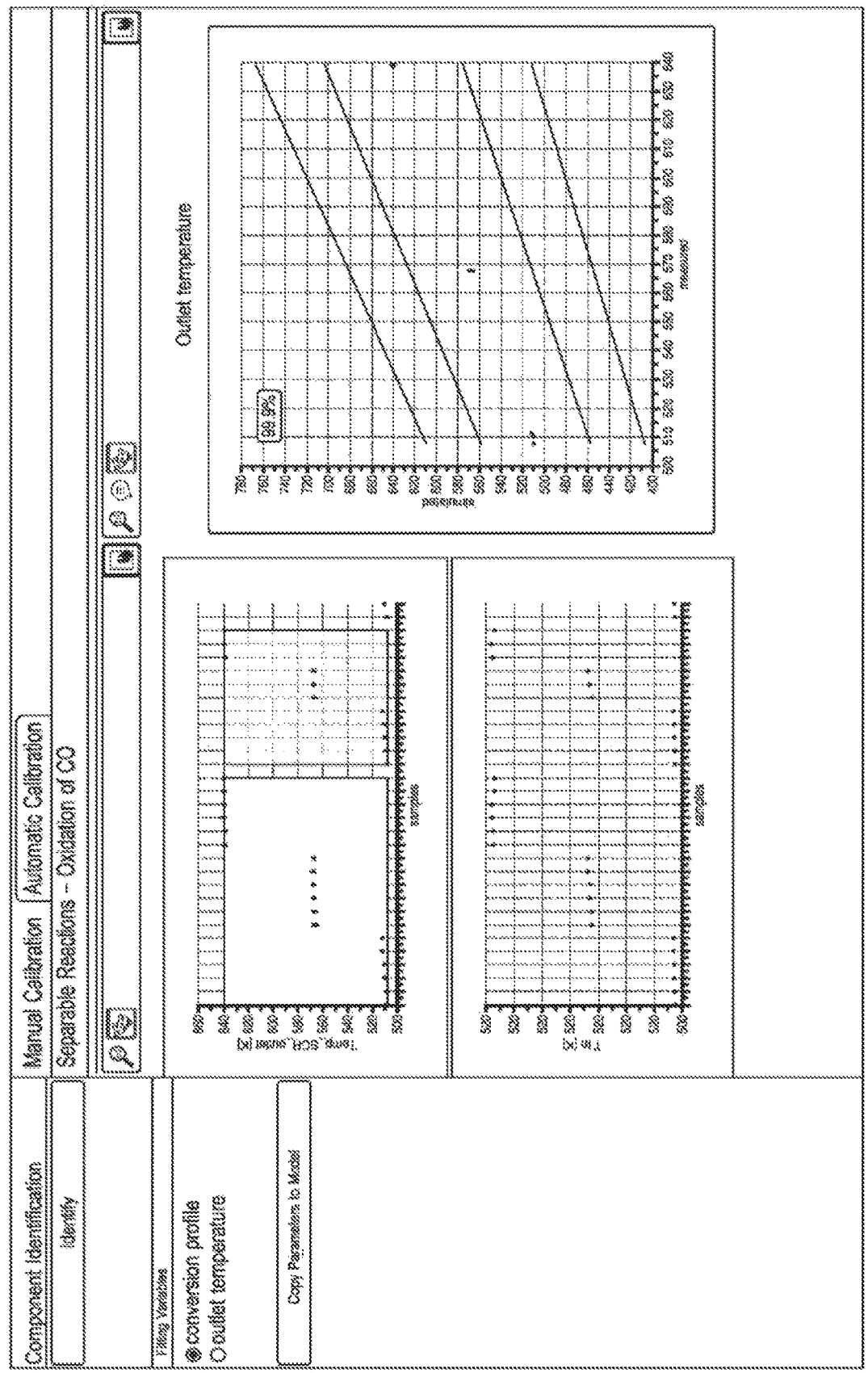
FIG. 16 is a diagram of a graph of a plot for separable reactions with manual calibration relative to outlet temperature.

FIG. 16 is a diagram of graph 59 of a plot for separable reactions with manual calibration relative to outlet temperature.

FIG. 17 is a diagram of a table 60 of parameters for not reactions of component level identification. They consist of groups of reactions that take place together. Parameters for identification may be just those that have not yet been identified. Parameters may incorporate pre-exponential factors, activation energies, reaction rate exponents, heat of reactions, diffusion parameters for velocity, and diffusion parameters for temperature. Parameters may also incorporate several possible custom functions inhibition parameters, which are parameters used just for DOC if the inhibition is on, or some selection if it should be used.

Figure 18:
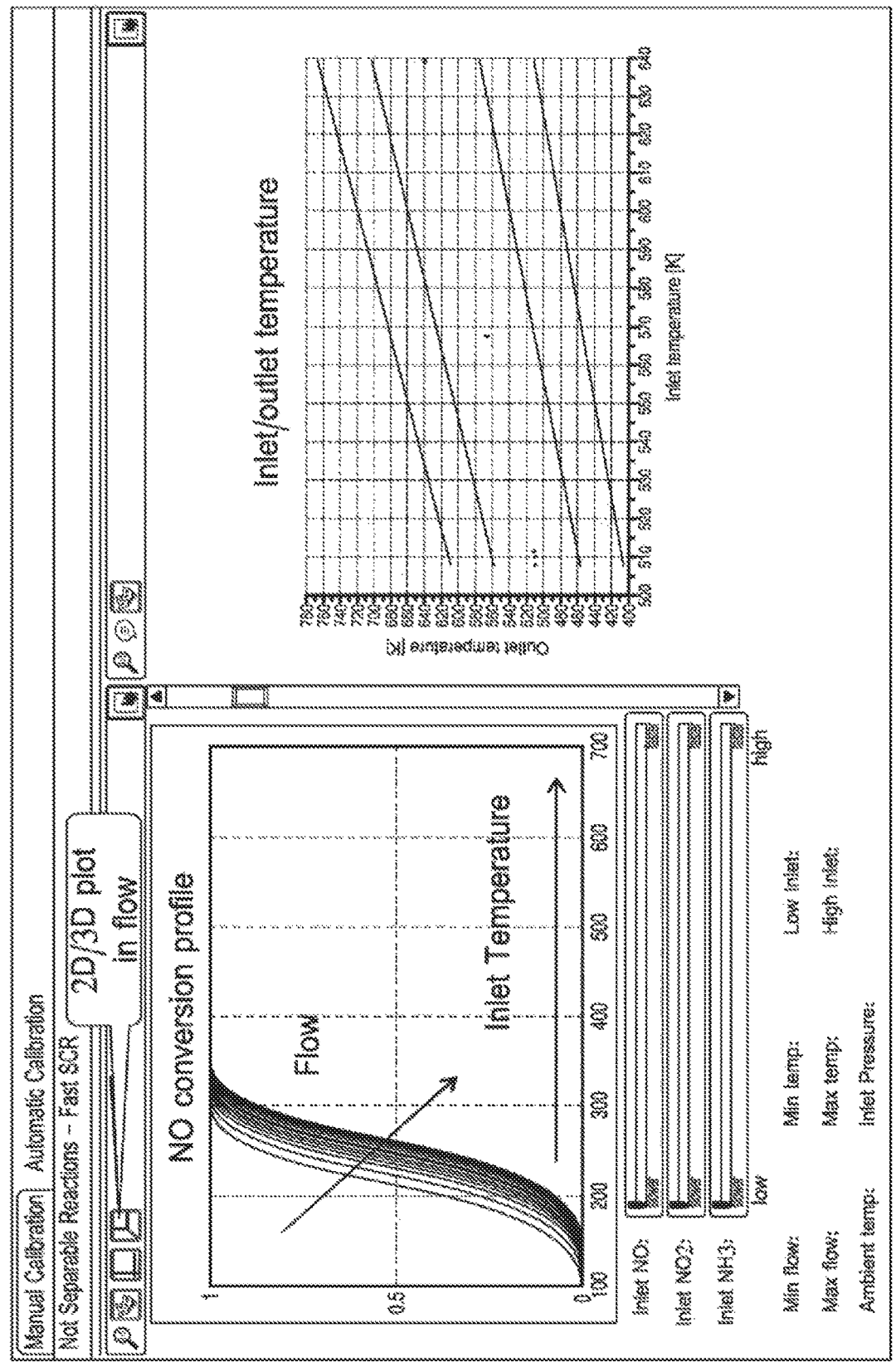
FIGS. 18, 19 and 20 are diagrams of plots each group of not separable reactions with manual calibration for a component level identification involving conversion files for NO, NO2 and NH3, respectively.
Figure 19:
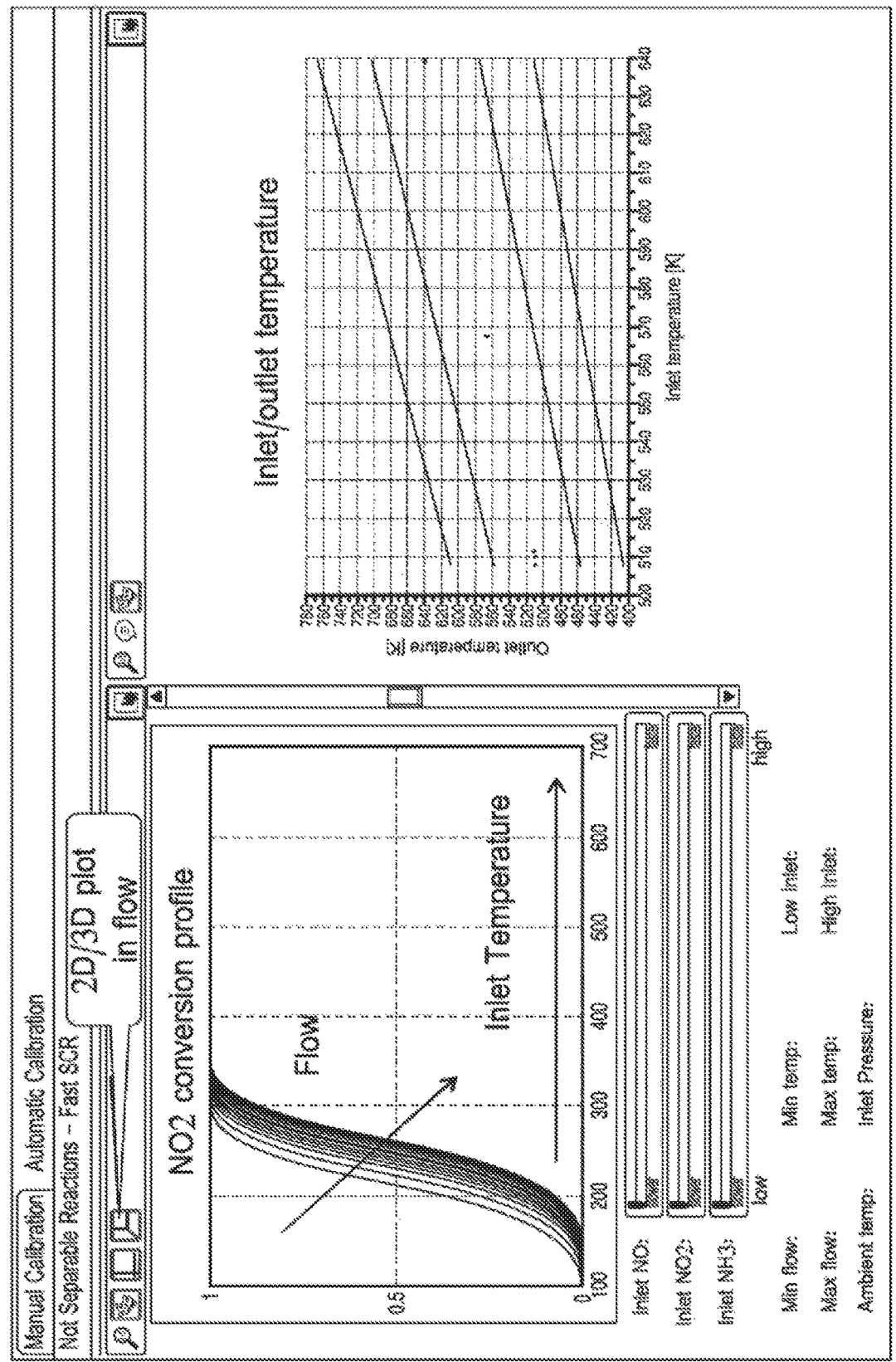
Figure 20:
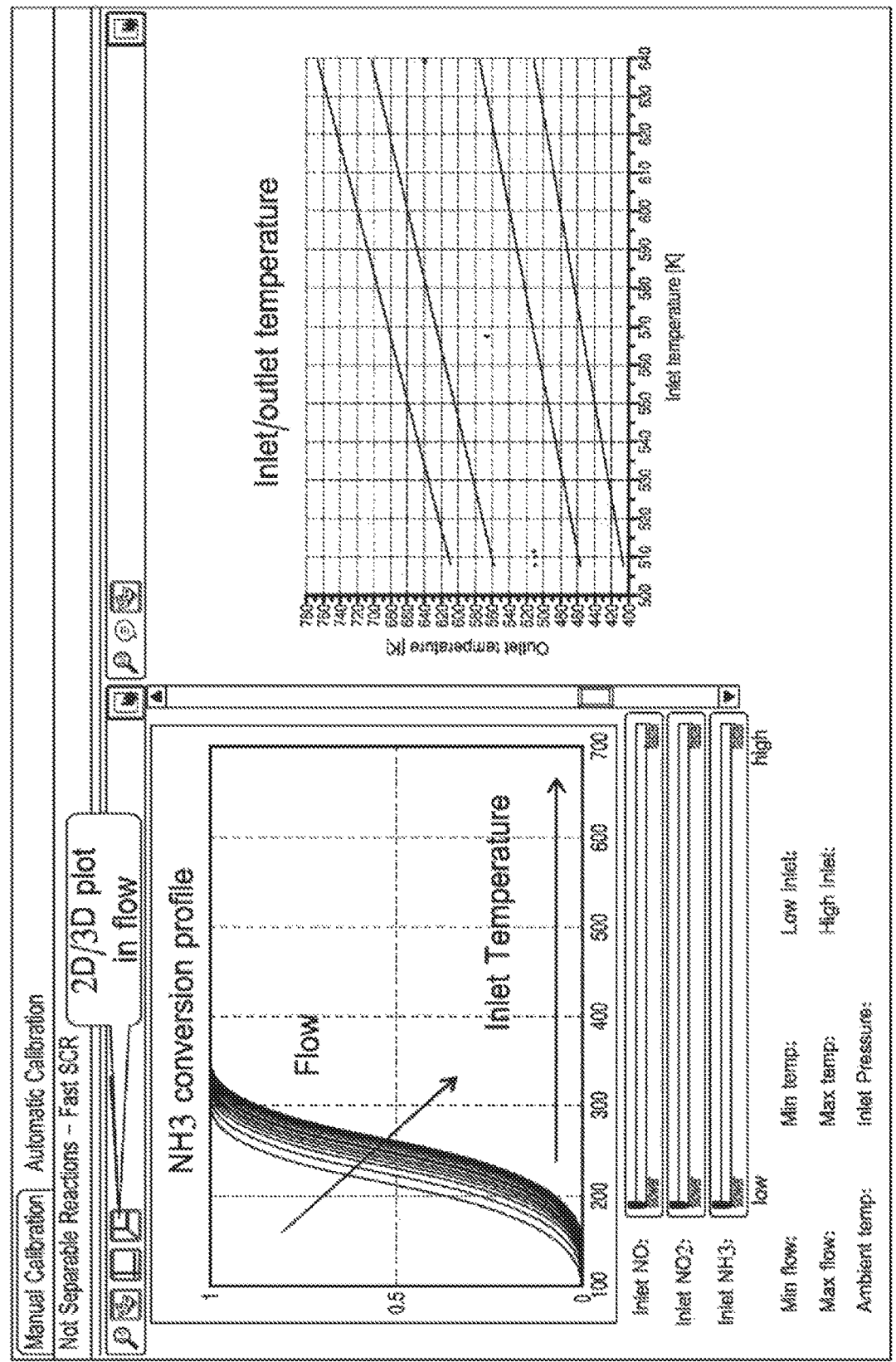

Component level identification may be pursued in a case of non-separable reactions (groups) that may have sets of steady-state flow bench data. There may be an efficiency curve for a particular reaction. Signals that may be needed may incorporate inlet/outlet temperature, inlet pressure, inlet flow, inlet concentration of species participating in reactions, and ambient temperature. An identification process may be steady state. FIGS. 18, 19 and 20 are diagrams of plots 61, 62 and 63 for each group of separable reactions with manual calibration for component level identification involving conversion files for NO, NO2 and NH3, respectively.

Figure 21:
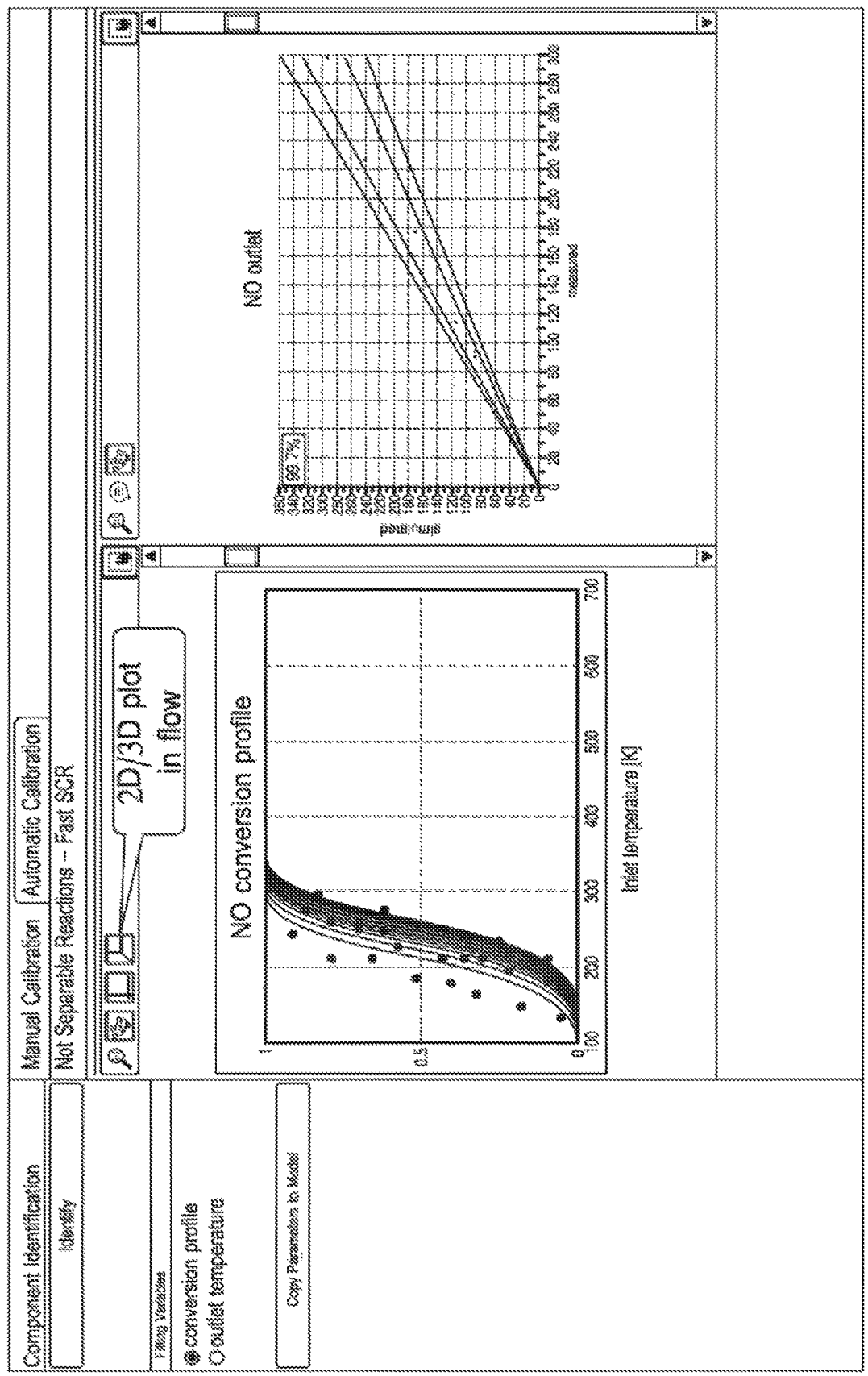
FIGS. 21, 22 and 23 are diagrams of plots for each group of not separable reactions with automatic calibration for a component level identification involving conversion profiles for NO, NO2 and NH3.
Figure 22:
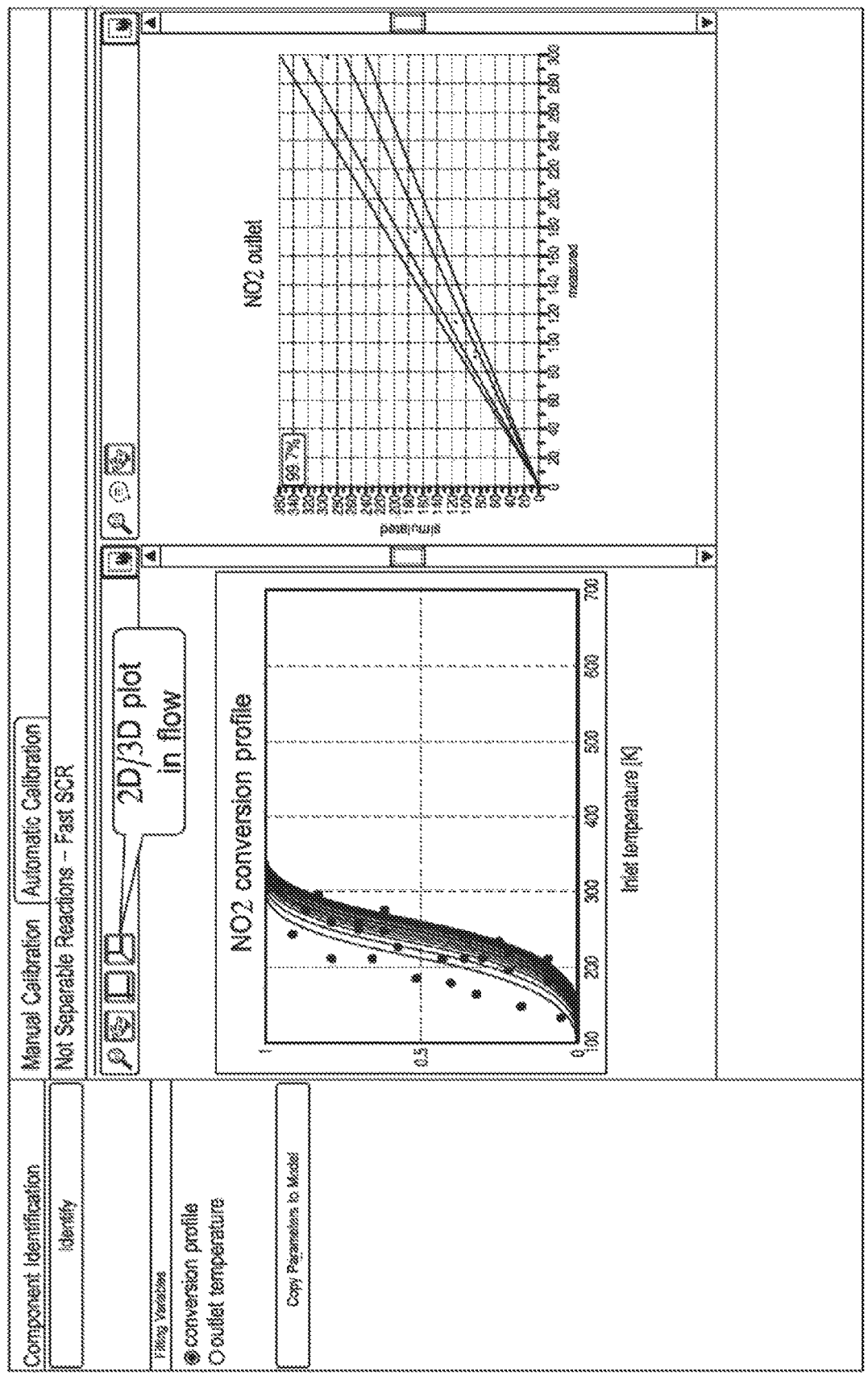
Figure 23:
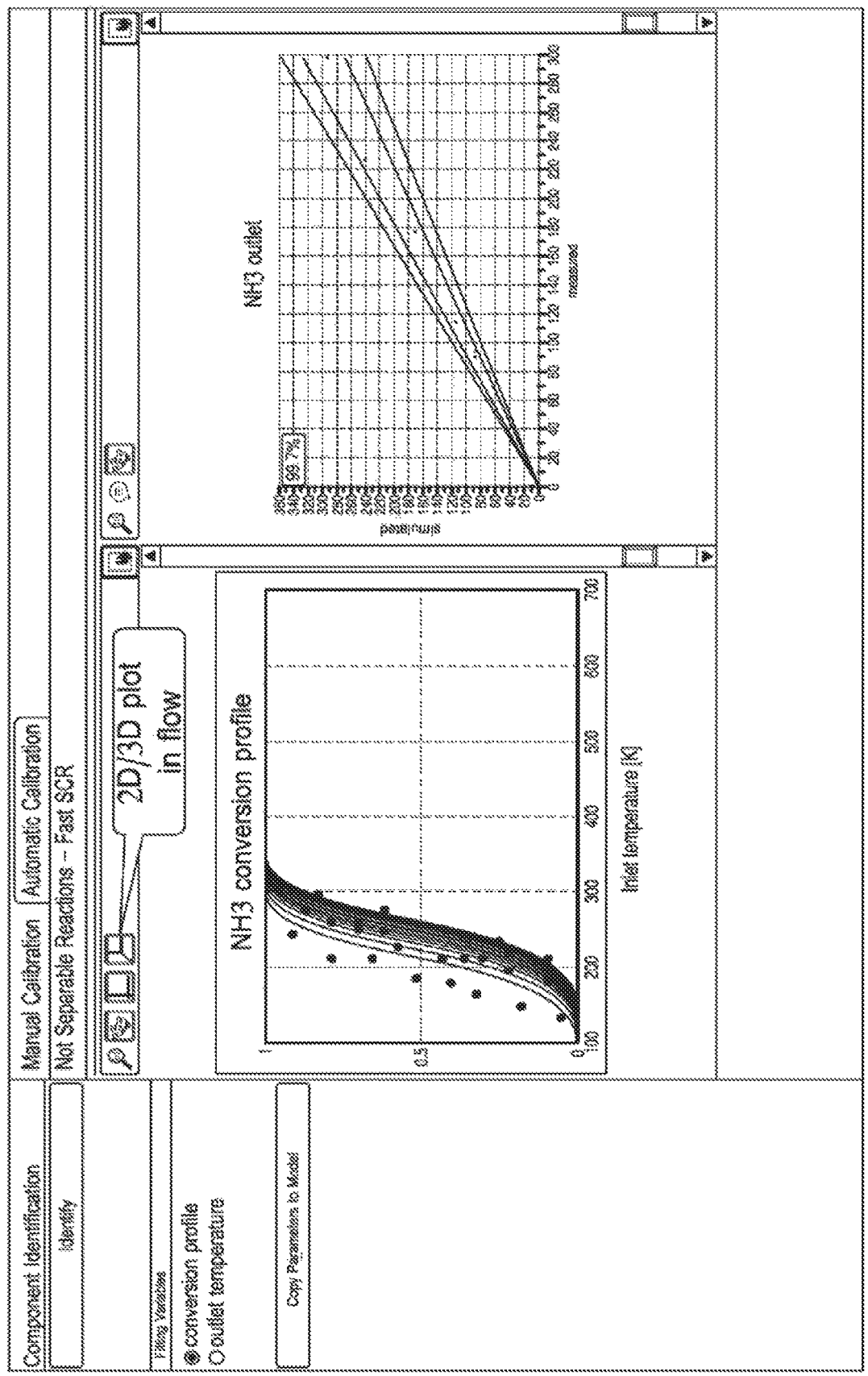
Figure 24:
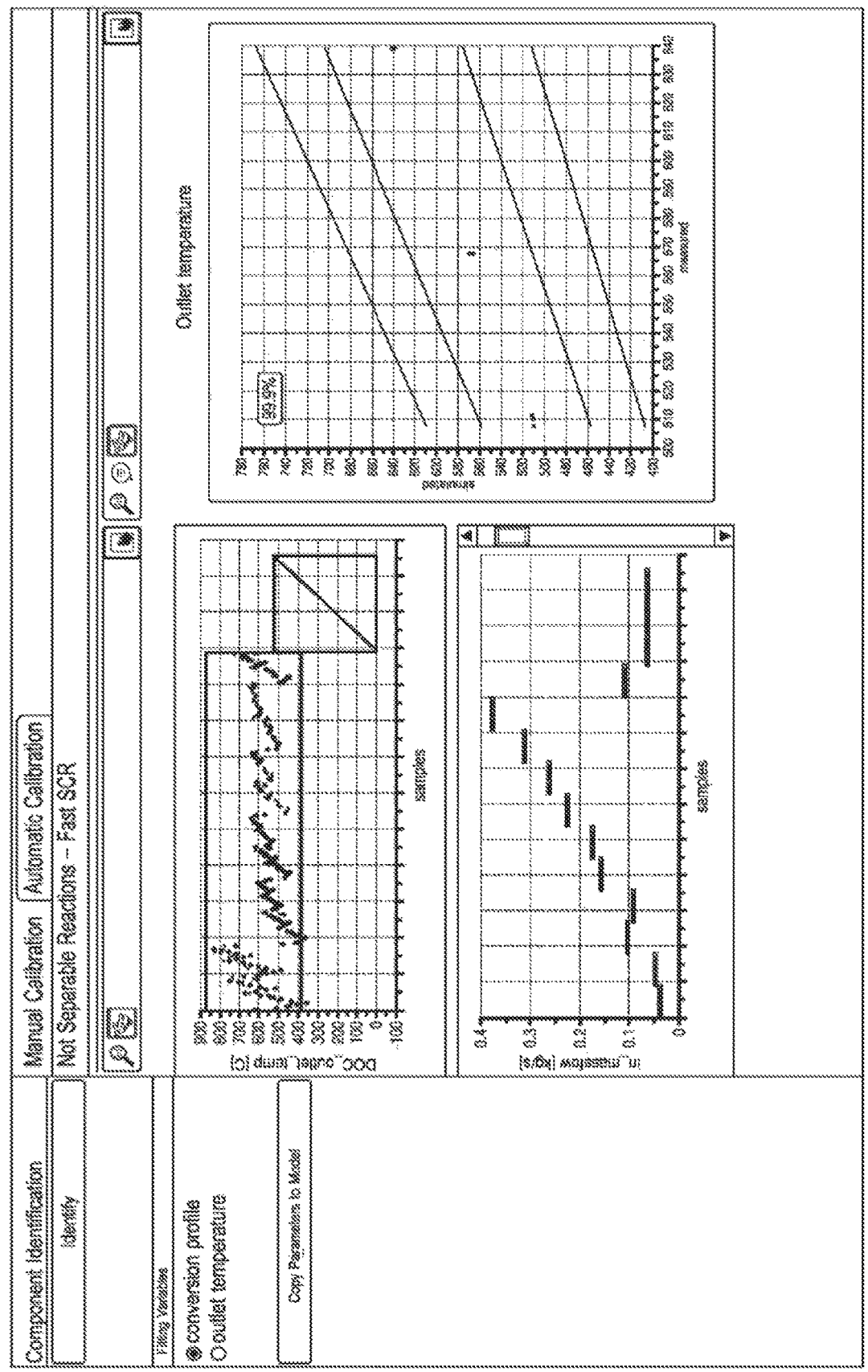
FIG. 24 is a diagram of graphs for not separable reactions with automatic calibration relative to outlet temperature.

FIGS. 21, 22 and 23 are diagrams of plots 64, 65 and 66 for each group of not separable reactions with automatic calibration for component level identification involving conversion profiles for NO, NO2 and NH3. FIG. 24 is a diagram of graphs 67 for not separable reactions with automatic calibration relative to outlet temperature.

Catalyst implementation may be noted. The catalyst may be of a continuous model, general enough to handle virtually any kind of reactions, be a MATLAB C-MEX S-function, have many parameters for identification, and have many parameters fixed for chosen chemical reactions.

The same block (MATLAB S-function) may be used for SCR, SCRF, DOC and the like. Just configuration and user data may be different.

Catalyst implementation may be noted. A nonlinear continuous 1D model that can handle any kind of reactions may be used. A MATLAB C-MEX S-function may be incorporated. Cca 30 parameters may be used for identification. Many parameters may be fixed for chosen chemical reactions. The parameters may be saved in block's user data.

Figure 25:
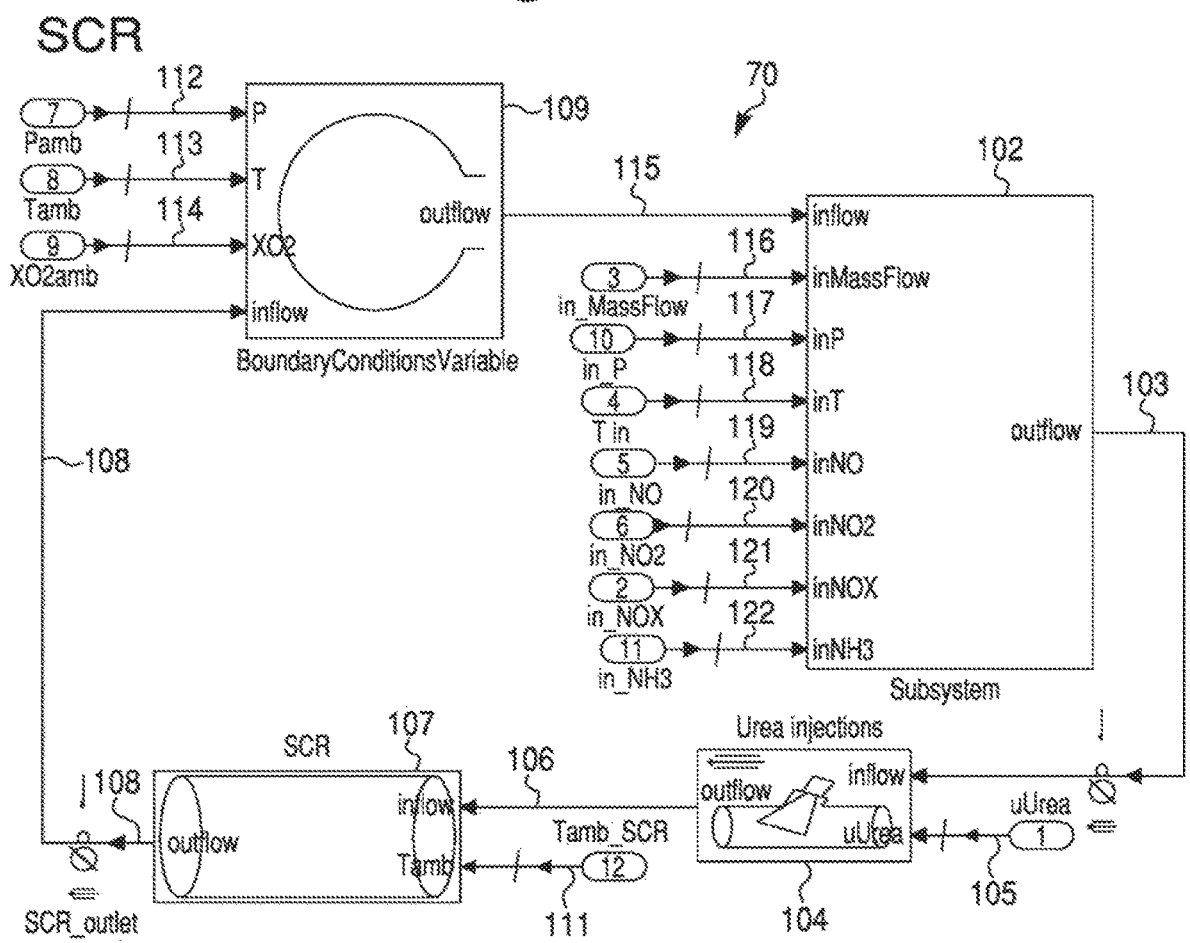
FIG. 25 is a diagram of a block layout for SCR.

FIG. 25 is a diagram of a block layout 70 for SCR. A subsystem 102 may represent engine exhaust with an outflow 103 to a urea injector 104. Urea 105 may be provided as an inflow to injector 104. A resulting outflow 106 may consist of NH3 as an inflow to an SCR component 107. An additional input 111 of catalyst surrounding temperature may go to SCR component 107. Component 107 may have an outflow 108 of NH3 provided as inflow to a modified boundary block 109 with NO, NO2, HC, and NH3 signals. An ambient pressure 112, ambient temperature 113 and ambient oxygen mass fraction (XO2) 114 may be input to modified boundary block 109. An outflow 115 from block 109 may go subsystem 102. In mass flow 116, in pressure 117, in temperature 118, in NO 119, in NO2 120 in NOx 121 and in NH3 122 may go to subsystem 102.

Figure 26:
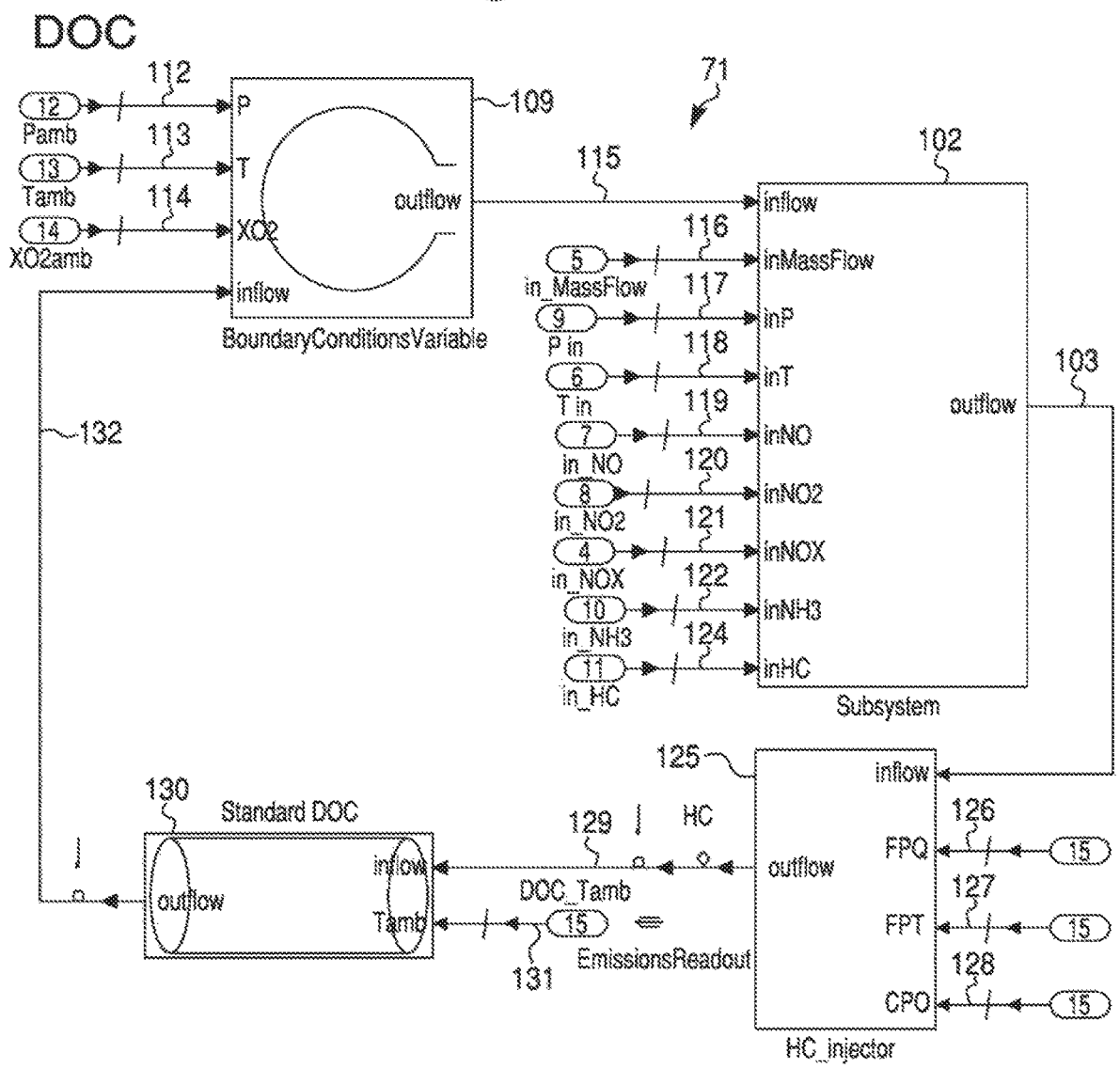
FIG. 26 is a diagram of a block layout for DOC.

FIG. 26 is a diagram of a block layout 71 for DOC. A subsystem 102 may represent engine exhaust with an outflow 103 to an HC injector 125. A far post quantity (FPQ) 126, a far post timing (FPT) 127 and a close post quantity (CPQ) 128 may be input to HC injector 125. A resulting outflow 129 may consist of HC as an inflow to a standard DOC component 130. An additional input 131 of catalyst surrounding temperature may go to DOC component 130. Component 130 may have an outflow 132 of HC provided as inflow to a modified boundary block 109 with NO, NO2, HC, and NH3 signals. An ambient pressure 112, ambient temperature 113 and ambient O2 fraction 114 may be input to modified boundary block 109. An outflow 115 from block 109 may go subsystem 102. In mass flow 116, in pressure 117, in temperature 118, in NO 119, in NO2 120 in NOx 121, in NH3 122, and in HC 124 may go to subsystem 102.

Figure 27:
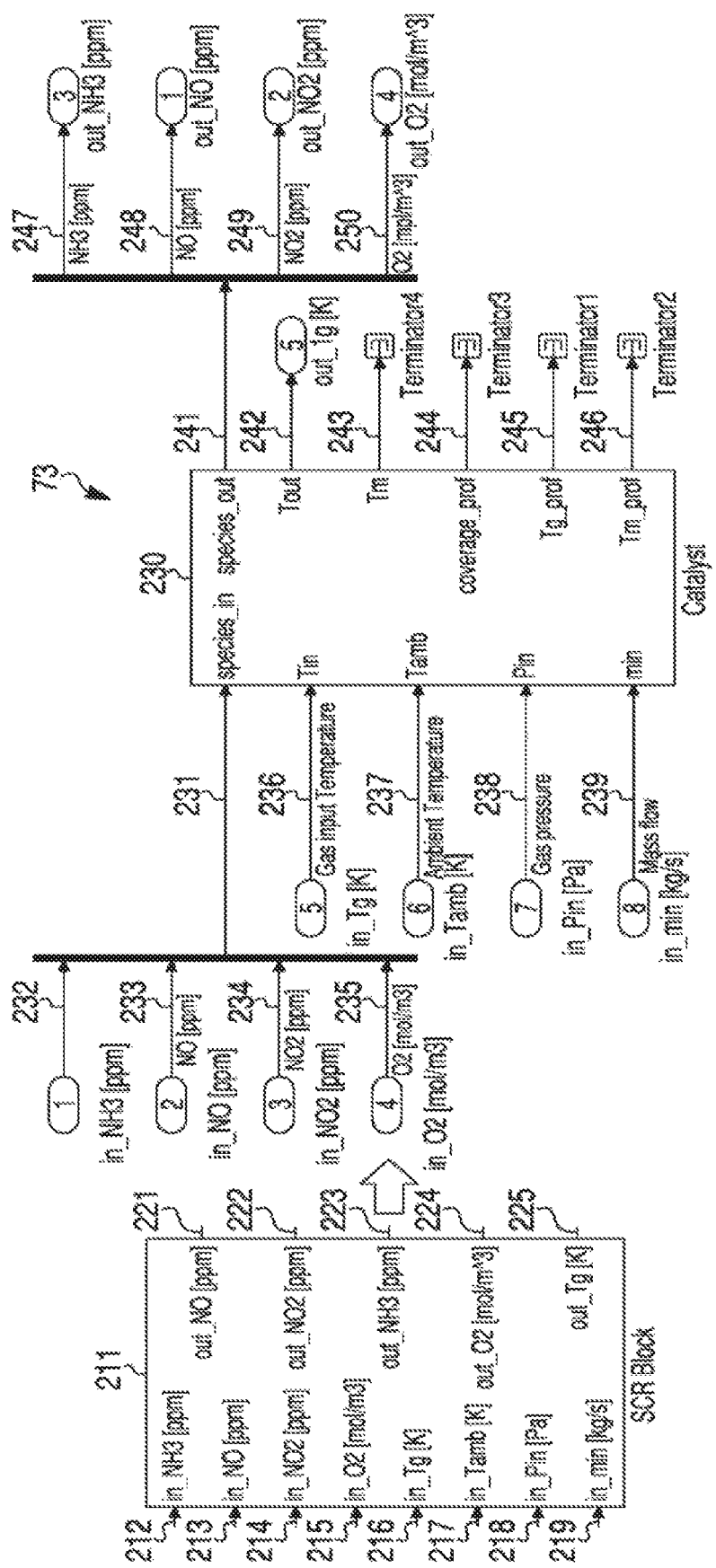
FIG. 27 is a diagram of a SCR block showing inputs and outputs.

SCR block 211 of diagram 73 in FIG. 27 may have inputs 212, 213, 214, 215, 216, 217, 218 and 219 corresponding to NH3, NO, NO2, O2, gas temperature (Tg), ambient temperature (Tamb), inlet pressure (Pin) and mass flow (Min), respectively. SCR block 211 may have outputs 221, 222, 223, 224 and 225 corresponding to NO, NO2, NH3, O2 and outlet gas temperature (Tg), respectively. A species input 231 to a catalyst 230 may incorporate inputs 232, 233, 234 and 235 corresponding to NH3, NO, NO2 and O2, respectively. Other inputs of catalyst 230 may incorporate gas input temperature 236, ambient temperature 237, gas pressure 238 and mass flow 239. Outputs of catalyst 230 may incorporate a species out 241, gas temperature out 242, monolith temperature out 243, coverage profile out 244, a gas temperature profile along axial direction of catalyst out 245, and monolith temperature profile along axial direction of catalyst out 246. Species out 241 may go to set of incorporating outputs 247, 248, 249 and 250 corresponding to NH3, NO, NO2 and O2, respectively.

Figure 28:
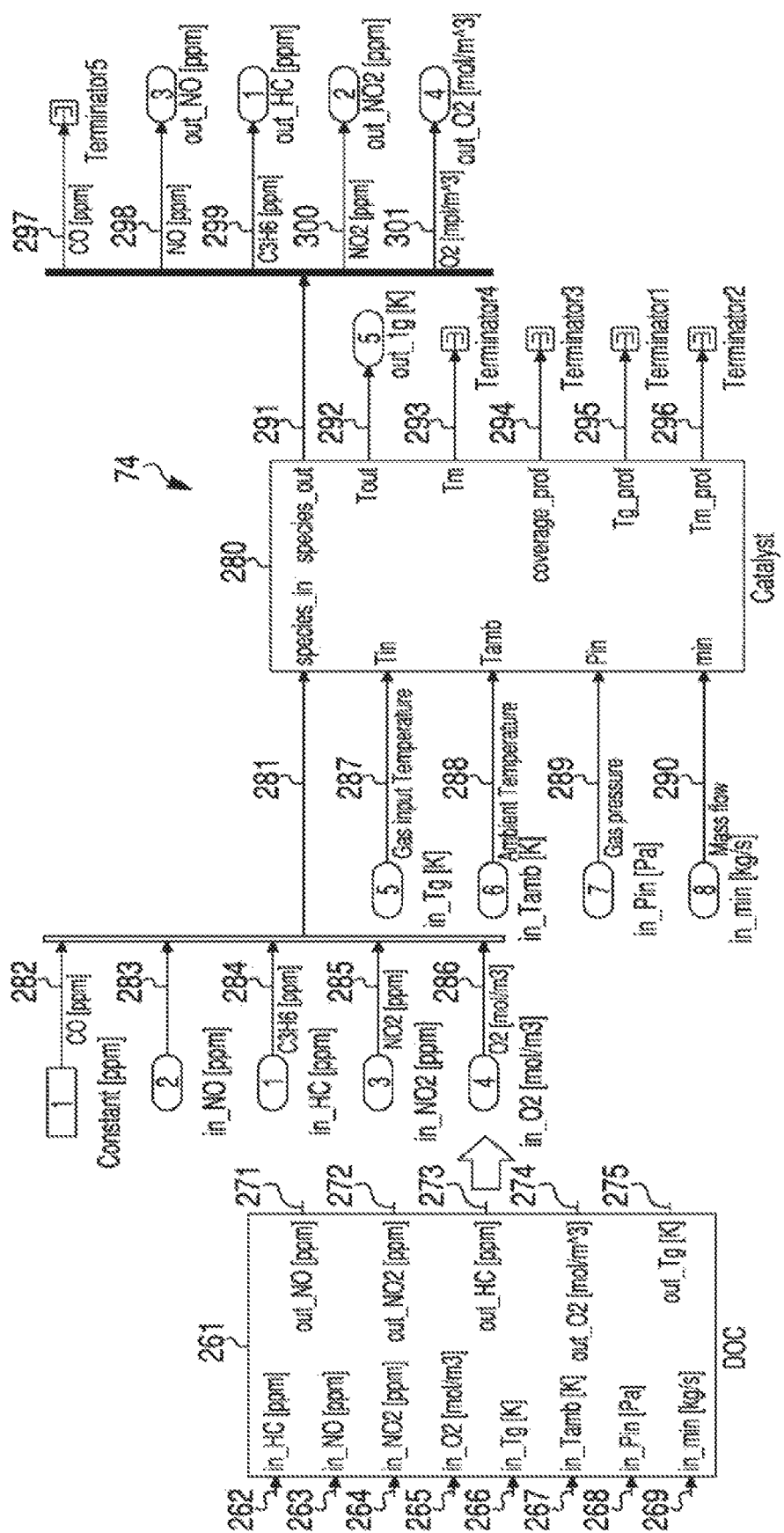
FIG. 28 is a diagram of a DOC block showing inputs and outputs.

DOC block 261 of diagram 74 in FIG. 28 may have inputs 262, 263, 264, 265, 266, 267, 268 and 269 corresponding to HC, NO, NO2, O2, inlet gas temperature (Tg), ambient temperature (Tamb), inlet pressure (Pin) and inlet mass flow (Min), respectively. DOC block 261 may have outputs 271, 272, 273, 274 and 275 corresponding to NO, NO2, HC, O2 and outlet gas temperature (Tg), respectively.

A species input to a catalyst 280 may incorporate inputs 282, 283, 284, 285 and 286 corresponding to CO which may be assumed as constant, NO, CH (C3H6), NO2, and O2, respectively. Other inputs of catalyst 280 may incorporate gas input temperatures 287, ambient temperature 288, gas pressure 289, and mass flow 290. Outputs of catalyst 280 may incorporate species out 291, temperature out 292, monolith temperature out 293, coverage profile along axial direction of catalyst out 294, a gas temperature profile along axial direction of catalyst out 295, and a monolithtemperature profile along axial direction of catalyst 296. Species out 291 may go to set of incorporating outputs 297, 298, 299, 300 and 301 corresponding to CO to terminator 8, NO, HC (C3H6), NO2 and O2, respectively.

FIG. 29 is a diagram of a table 75 of parameters for a system level identification. The table of parameters may incorporate frontal flow area, catalyst effective volume, heat transfer correction factor from gas to monolith, specific heat of monolith, adsorption pre-exponential factors, adsorption rate exponents, desorption pre-exponential factors, desorption activation energies, catalyst capacity (sites), pre-exponential factors, activation energies, reaction rate exponents, heat of reactions, diffusion parameters for velocity, diffusion parameters for temperature, inhibition parameters of a custom function 1, and inhibition parameter of a custom function 2. Adsorption rate exponents may be currently assumed as fixed and not used for identification. The specific heat of monolith and catalyst capacity may influence just a dynamic response.

Figure 30:
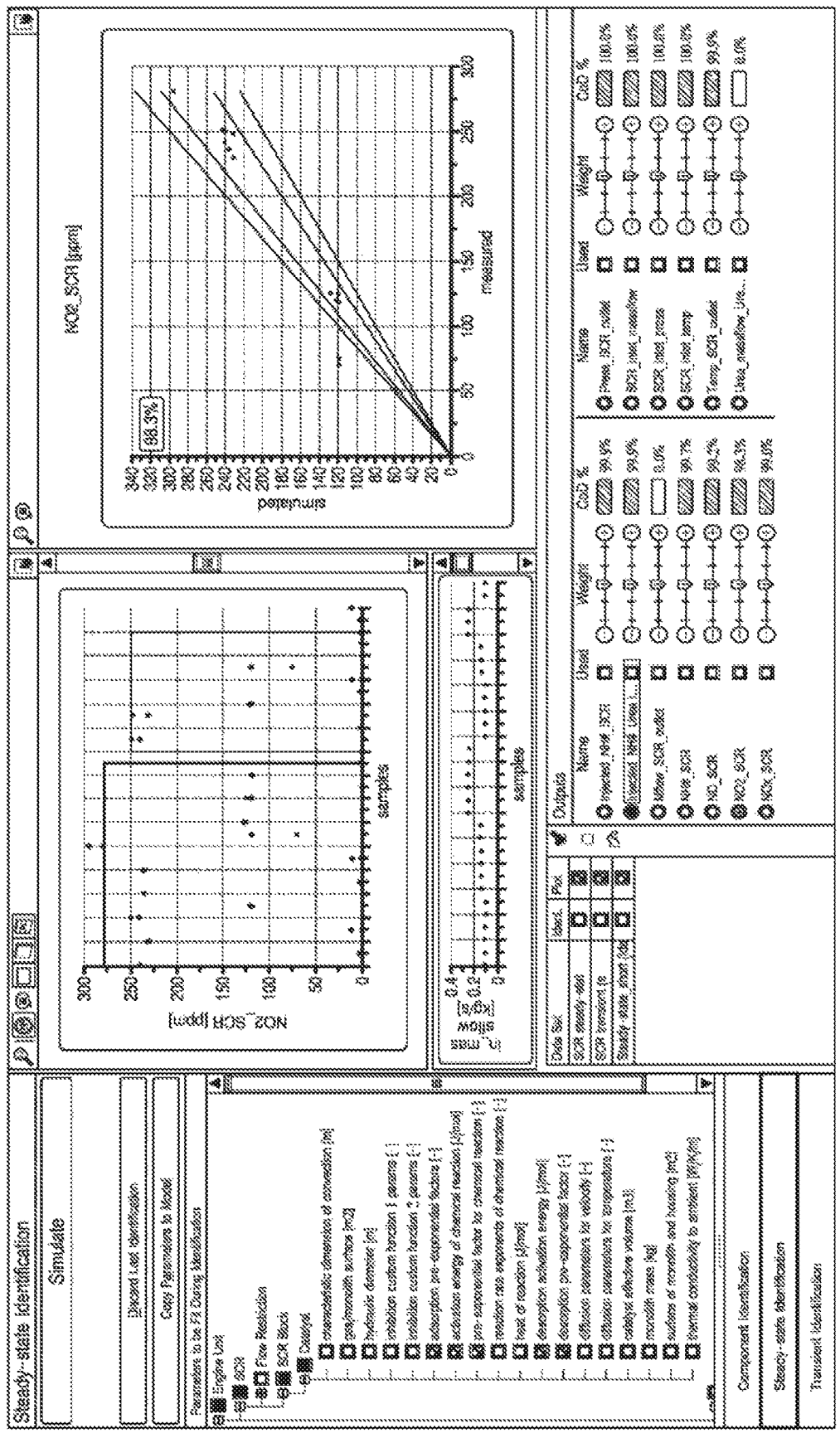
FIG. 30 is a diagram of a navigation tree, table and graphs for an SCR steady-state data fit.

FIG. 30 is a diagram of a set 76 of a navigation tree, table and graphs for an SCR steady-state data fit.

Figure 31:
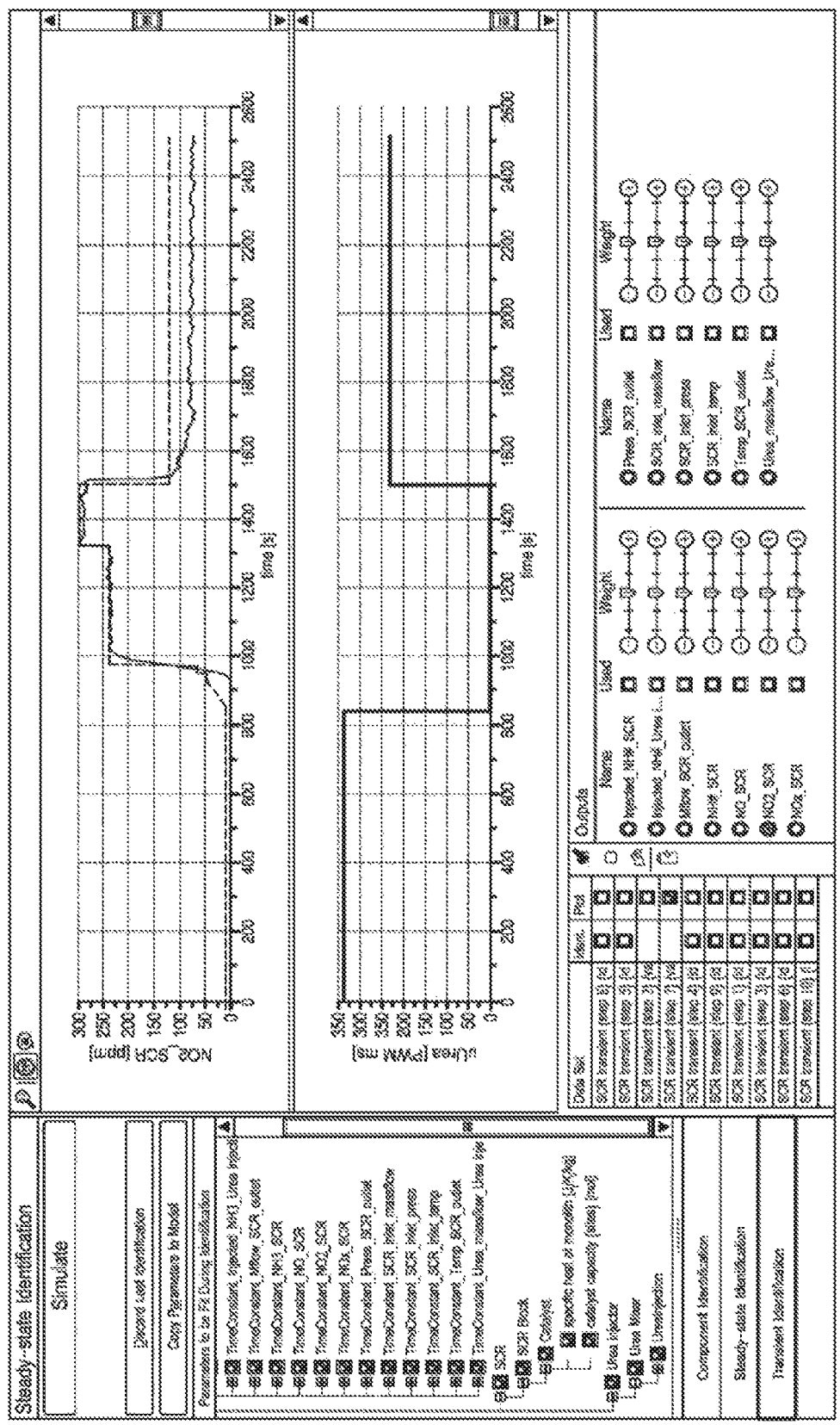
FIG. 31 is a diagram of a navigation tree, table and graphs for an SCR transient data fit.

FIG. 31 is a diagram of a set 77 of a navigation tree, table and graphs for an SCR transient data fit.

Figure 32:
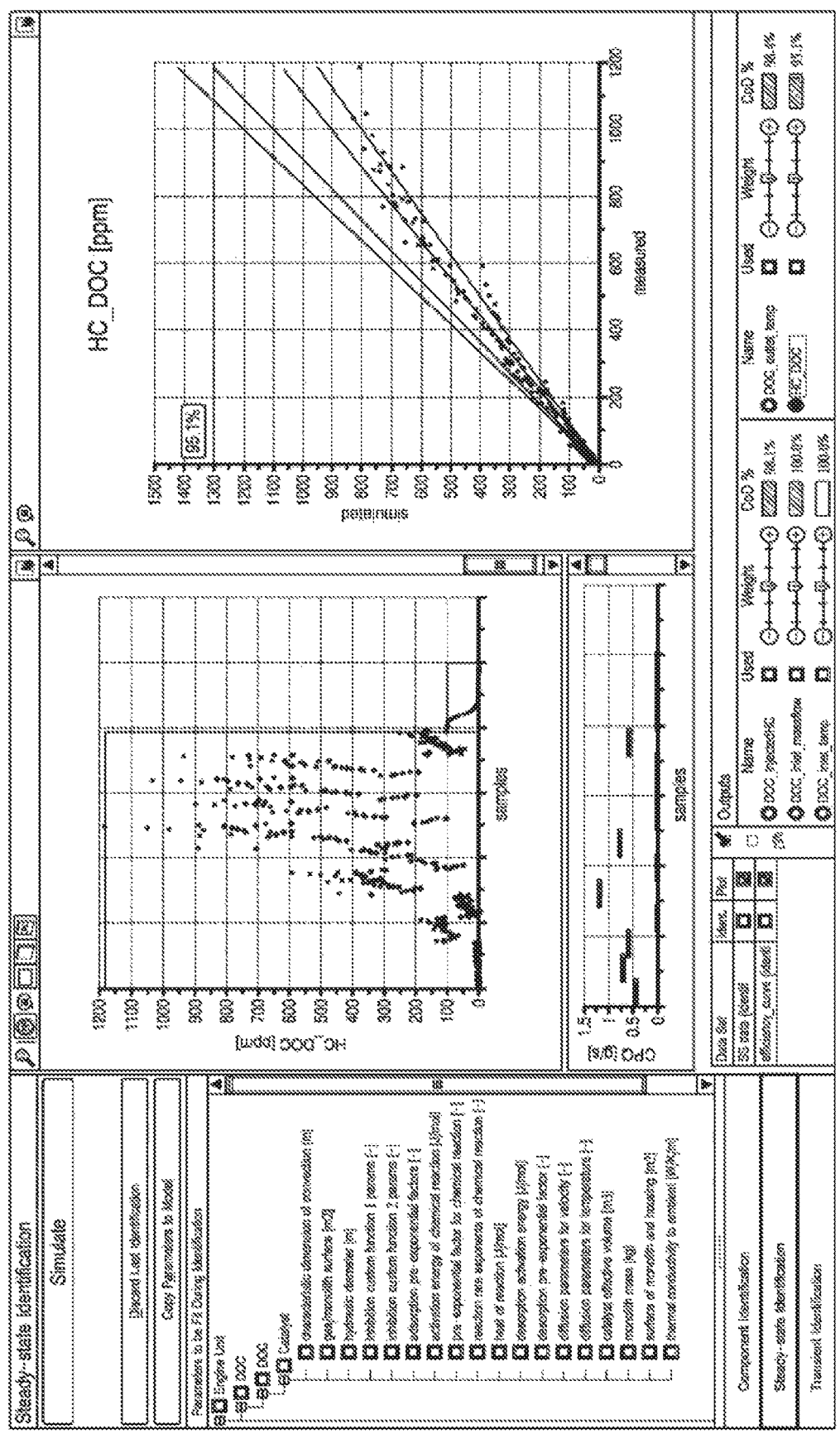
FIG. 32 is a diagram of a navigation tree, table and graphs for a DOC steady-state data fit.

FIG. 32 is a diagram of a set 78 of a navigation tree, table and graphs for a DOC steady-state data fit.

Figure 33:
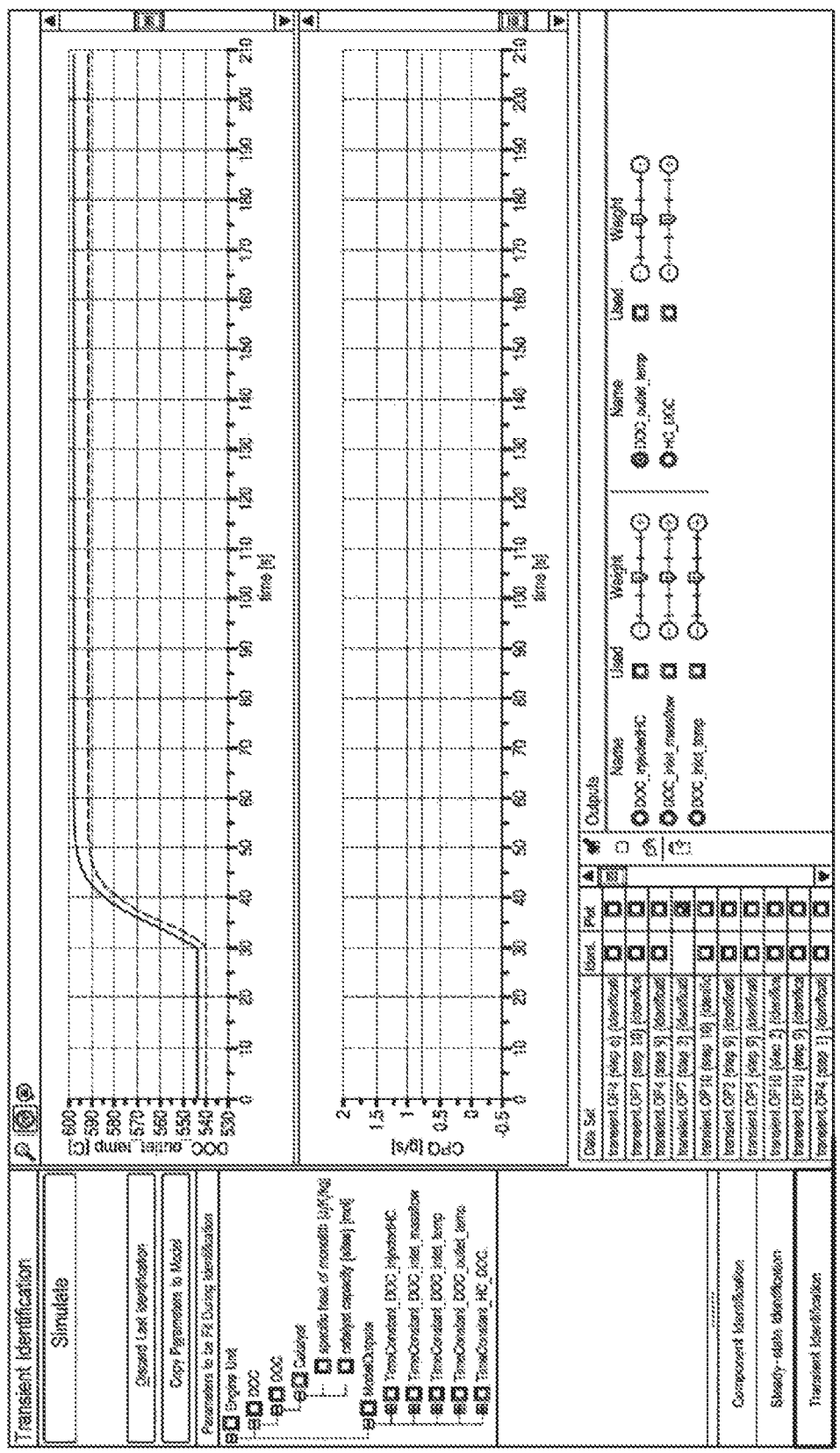
FIG. 33 is a diagram of a navigation tree, table and graphs for a DOC transient data fit.

FIG. 33 is a diagram of a set 79 of a navigation tree, table and graphs for a DOC transient data fit.

To recap, an identification apparatus may incorporate a catalyst device for an engine, and a catalyst model of the catalyst device having a thermal model component, an adsorption and desorption component, a chemical reaction component, and a global component.

The thermal model component may represent heat transfer of the catalyst device, selected from a group consisting of heat transfer from gas to monolith, heat transfer from monolith to housing, and heat transfer from housing to ambient. The adsorption and desorption component may incorporate a storage of chemical species for reaction. The chemical reaction component may incorporate a reaction mechanism for chemical reactions.

Parameters for the catalyst model may be determined. Values of the parameters may be determined. Parameters of the thermal model may have values that are automatically estimated from data of on-engine or flow bench with reaction heat suppressed.

The adsorption and desorption of the adsorption and desorption component may be estimated independently when bench flow data are available but are estimated together with virtually all chemical reactions. The chemical reaction component may incorporate separable chemical reactions in that each chemical reaction can be isolated from the others during an identification process in that one reaction takes place at a time.

The chemical reaction component can further incorporate one or more inseparable chemical reactions.

Steady state data may be used in an identification. The identification based on steady state data may be an estimate for an identification based on transient data. Transient data may be used in an identification.

An approach for catalyst model identification may incorporate developing a catalyst model, processing a first phase having a specification of initial values for one or more parameters of the catalyst model, processing a second phase having a component level identification, and processing a third phase having a system level identification. The first, second and third phases may be processed by a computer.

Component level identification may incorporate a thermal model, adsorption and desorption, and chemical reactions. If there is one pollutant in a chemical reaction, then the chemical reaction may be of one component and parameters of the component that can be identified independently on other components from chemical flow bench data.

Developing the catalyst model may incorporate configuring the catalyst model with virtually all needed components for an engine application. The specification of initial values for one or more parameters of the catalyst model may incorporate estimating the initial values of virtually all needed parameters and selecting catalyst model components. System level identification may incorporate performing identification of the catalyst model to obtain a final set of parameters of the catalyst model.

Component level identification may incorporate steady state identification and transient identification. System level identification may incorporate steady state identification and transient identification.

A catalyst modeling mechanism may incorporate a computer, an engine from which an engine model is developed and stored in the computer, and a catalyst device, connected to the engine, from which a catalyst model is developed and stored in the computer.

The modeling may be accomplished by an identification procedure. The identification procedure may incorporate a catalyst parameter identification procedure. The catalyst parameter identification procedure may incorporate determination of parameters for the catalyst device, specification of values for the parameters, component level identification, and system level identification.

Component level identification may incorporate steady state identification and transient identification. System level identification may incorporate steady state identification and transient identification.

Component level identification may be obtained from data of a flow bench that permits preparation of exhaust gas composition from the engine. System level identification may be obtained from data of the exhaust gas composition from the engine. Component level identification may be determined from data selected from a group consisting of on engine data.

Results of the component level identification may be used as a starting point for system level identification. System level identification of the catalyst model may be performed to get a final set of parameters of the catalyst model.

In the present specification, some of the matter may be of a hypothetical or prophetic nature although stated in another manner or tense.

Although the present system and/or approach has been described with respect to at least one illustrative example, many variations and modifications will become apparent to those skilled in the art upon reading the specification. It is therefore the intention that the appended claims be interpreted as broadly as possible in view of the related art to include all such variations and modifications.

What is claimed is:

1. A catalyst modeling mechanism comprising: a computer; an engine from which an engine model is developed and stored in the computer; and a catalyst device, connected to the engine, from which a catalyst model is developed and stored in the computer; and wherein:
    the computer is configured to construct the catalyst model by an identification procedure;
    the identification procedure comprises a catalyst parameter identification procedure, which the computer is configured to perform by:
    determining catalyst parameters for the catalyst device;
    specifying initial values for the catalyst parameters;
    identifying components from flow bench data that permits preparation of exhaust gas composition from the engine; and
    identifying system level details from data of the exhaust gas composition from the engine, using the identified components from flow bench data as a starting point for identifying system level details; further wherein a final set of parameters of the catalyst model is generated from the identifying of system level details.

2. The mechanism of claim 1, wherein: component level identification comprises steady state identification and transient identification; and system level identification comprises steady state identification and transient identification.

3. A vehicle comprising the catalyst modeling mechanism of claim 1, including each of the engine and catalyst device, and an engine control unit, the engine control unit being configure to apply the catalyst model operate the engine and the catalyst device to prevent release of a contaminant the catalyst device is configured to react with.

4. A method of catalyst modeling in a system that includes each of a computer; an engine from which an engine model is developed and stored in the computer; and a catalyst device, connected to the engine, from which a catalyst model is developed and stored in the computer; the method comprising using an identification procedure to accomplish the modelling, the identification procedure including a catalyst parameter identification procedure which comprises:
    determining catalyst parameters for the catalyst device;

specifying initial values for the catalyst parameters;
identifying components from flow bench data that permits preparation of exhaust gas composition from the engine;
identifying system level details from data of the exhaust gas composition from the engine, using the identified components from flow bench data as a starting point for identifying system level details; and
generating a final set of parameters of the catalyst model from the identifying of system level details.

5. The method of claim 4, wherein:
component level identification comprises steady state identification and transient identification; and
system level identification comprises steady state identification and transient identification.

6. The method of claim 4, further comprising controlling operation of the catalyst device and engine using the computer by applying the catalyst model to prevent release of a contaminant the catalyst device is configured to react with.

* * * * *